(12) United States Patent
Oddo

(10) Patent No.: US 11,559,652 B2
(45) Date of Patent: Jan. 24, 2023

(54) OXYGEN DELIVERY APPARATUS USING EYEGLASS FRAMES

(71) Applicant: Aires Medical LLC, Ann Arbor, MI (US)

(72) Inventor: Nicholas Leonard Oddo, Ann Arbor, MI (US)

(73) Assignee: Aires Medical LLC, Ann Arbor, MI (US)

( * ) Notice: Subject to any disclaimer, the term of this patent is extended or adjusted under 35 U.S.C. 154(b) by 763 days.

(21) Appl. No.: 16/522,048

(22) Filed: Jul. 25, 2019

(65) Prior Publication Data

US 2020/0101252 A1    Apr. 2, 2020

Related U.S. Application Data

(60) Provisional application No. 62/738,362, filed on Sep. 28, 2018.

(51) Int. Cl.
```
A61M 16/06      (2006.01)
G02C 5/00       (2006.01)
G02C 11/00      (2006.01)
```
(52) U.S. Cl.
CPC ......... *A61M 16/0672* (2014.02); *G02C 5/001* (2013.01); *G02C 11/00* (2013.01)

(58) Field of Classification Search
CPC ...... A61M 16/0672; A61M 2016/0661; A61M 2202/0208; A61M 2207/00; A61M 2209/088; G02C 5/001; G02C 11/00; G02C 5/143; G02C 5/146; B33Y 80/00; B29L 2012/005
USPC .................. 128/200.24, 207.18; 351/41, 158
See application file for complete search history.

(56) References Cited

U.S. PATENT DOCUMENTS

| | | | |
|---|---|---|---|
| 3,209,755 A | * | 10/1965 | McCarthy ............. A61M 25/02 351/111 |
| 4,708,446 A | | 11/1987 | Timmons et al. |
| 5,193,534 A | | 3/1993 | Peppler |
| 6,772,762 B2 | | 8/2004 | Piesinger |

(Continued)

FOREIGN PATENT DOCUMENTS

WO    2017004600 A1    1/2017

OTHER PUBLICATIONS

"Oxy-View", http://www.oxyview.com/, accessed Jul. 24, 2019.

*Primary Examiner* — Tuyen Tra
(74) *Attorney, Agent, or Firm* — Caldwell Intellectual Property Law

(57) ABSTRACT

An oxygen delivery apparatus wearable by user includes a frame including nose pads connected to a bridge portion, an oxygen inlet defined by one of the nose pads, an oxygen inlet defined by the frame, and a hollow channel contained by the frame. The oxygen inlet and oxygen outlet are in fluid communication via the hollow channel. The frame can be formed as a monolithic structure using additive manufacturing. A nasal prong can be connected to the oxygen outlet such that a prong outlet of the prong is in fluid communication with the hollow channel. The prong outlet is positioned within a nostril of the user during use of the apparatus. A method of fabricating the frame includes obtaining measurement information for at least one of a head feature or facial characteristic of the user and generating a digital model of the oxygen delivery apparatus using the measurement information.

18 Claims, 8 Drawing Sheets

(56) References Cited

U.S. PATENT DOCUMENTS 6,886,562 B2     5/2005   Ishizuka
2008/0257343 A1   10/2008   Peterson \* cited by examiner

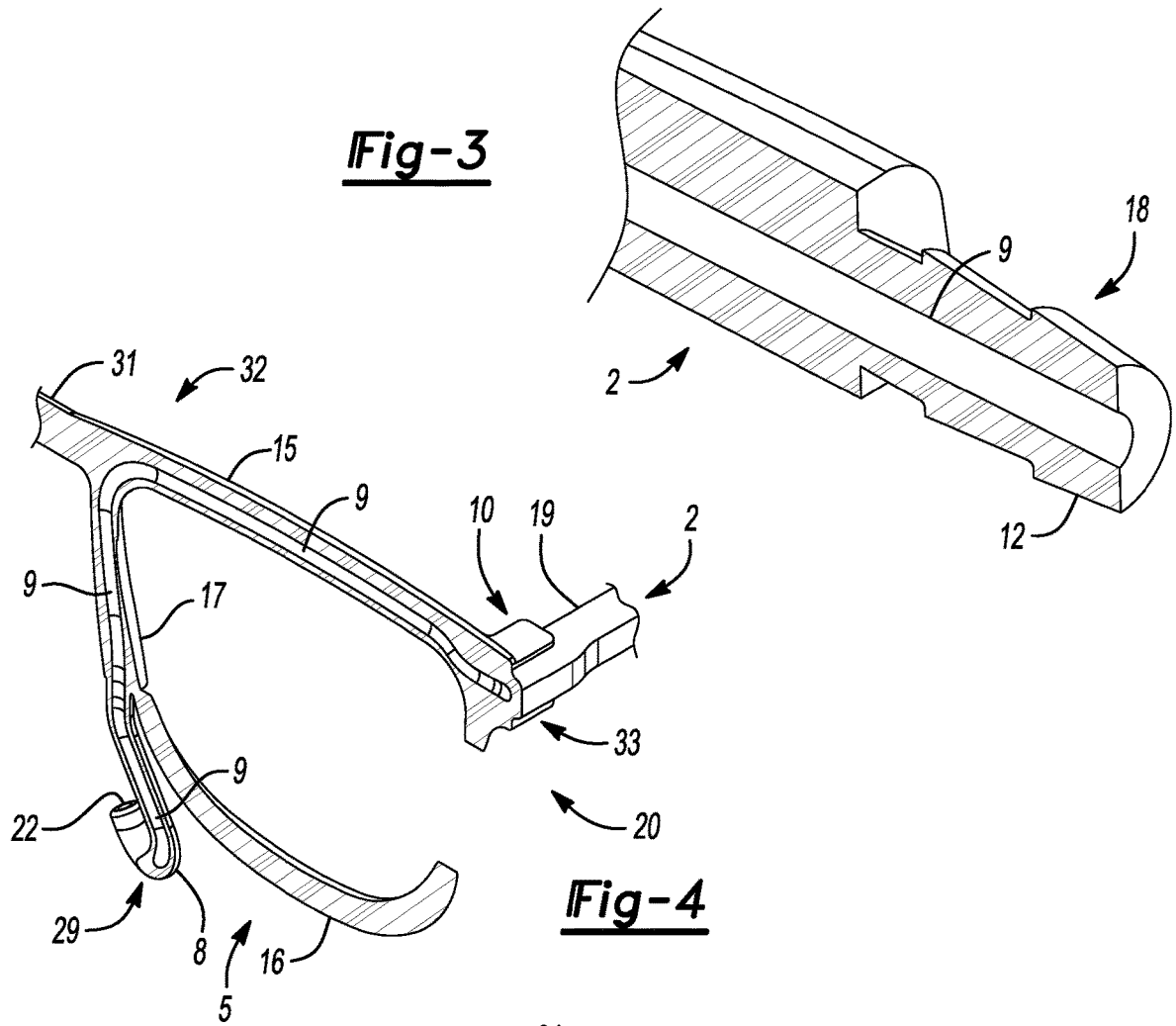
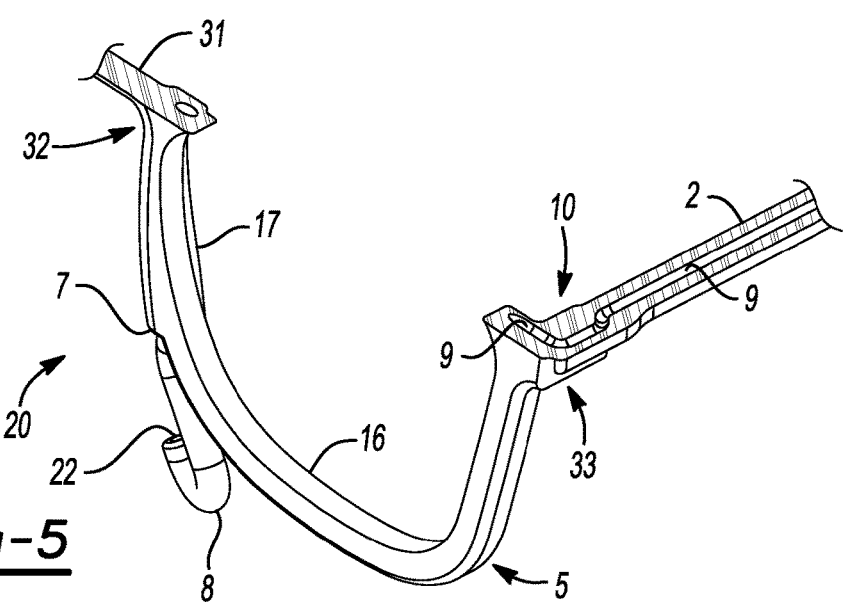

OXYGEN DELIVERY APPARATUS USING EYEGLASS FRAMES

CROSS-REFERENCE TO RELATED APPLICATIONS

This Application incorporates by reference U.S. Provisional Application 62/738,362 filed Sep. 28, 2018, in its entirety.

TECHNICAL FIELD

The present disclosure relates to the field of oxygen delivery apparatus and more specifically to oxygen delivery apparatus incorporating an eyeglass frame.

BACKGROUND

Traditionally people whose lungs have limited capacity have used supplemental oxygen as a therapy in order to improve their quality of life. This supplemental oxygen is supplied from an oxygen supply source such as an oxygen concentrator, which utilizes pressure swing adsorption to separate nitrogen from air to produce enriched oxygen continuously or via pulse dosage, or a pressurized oxygen tank. In prior art, this supplemental oxygen is delivered to the person using a pair of nasal cannulas, which comprises a tubular member that connects to the oxygen source and therein the oxygen flows through. This tubular member that connects to the oxygen source splits on one end into two separate tubular members and then two nasal prongs, and the nasal prongs are placed into the person's nostrils to deliver the oxygen to the person.

For many people, traditional nasal cannulas are uncomfortable and are aesthetically displeasing. Traditional nasal cannulas make it obvious that someone is using oxygen because the nasal cannula is usually hooked over the oxygen user's ears and runs across their face. Due to the negative stigma associated with oxygen use, oxygen users experience reduced self-esteem as a result and comply with prescribed oxygen therapy at a relatively low rate. In prior art, people have sought to hide nasal cannulas by passing tubing along the side or inserting tubing inside the eyeglass frame, as disclosed in U.S. Pat. No. 5,193,534. Because the outer diameter of the tubing is larger than the inner diameter of the tubing, this presents problems with oxygen flow if inserted inside the eyeglass frames as well as usability issues since it may be difficult for a person to insert or change out the tubing inside the eyeglass frames without special tools. This is also related to the fact that external tubing usually used with nasal cannulas needs to be replaced every few months to reduce the risk of bacterial infection. Because of the thin diameter of eyeglass frames, inserting tubing on the sides or inside the frame makes the eyeglass frame bulkier or presents manufacturing issues due to the thin walls, which limits the potential number of eyeglass frame designs.

Disclosed in U.S. Pat. No. 6,886,562 is a pair of spectacles in which oxygen can flow through without external tubing, wherein the frame itself is tubular and the two hinged joints are spring-loaded. These spectacles present numerous issues with sealing the flow of oxygen between the temple and lens housing portions of the frame, due to the use of spring-loaded hinged joints which cause frictional contact between the concave and convex connectors with the tubular members of the temple and lens housing portions, as well as manufacturing issues with utilizing different eyeglass designs since the entire eyeglass frame is tubular. This tubular frame is also undesirable for many consumers because this style of spectacles looks aesthetically similar to reading glasses.

SUMMARY

The present disclosure describes an oxygen delivery apparatus wherein oxygen flows through an eyeglass frame and is delivered through two nasal prongs that are attached to or an integral component of the eyeglass frame, with the goal of making oxygen use more comfortable and discreet than compared to traditional nasal cannulas, such that the oxygen delivery apparatus disclosed herein seeks to improve oxygen delivery apparatuses and solve problems associated with prior art solutions to oxygen delivery. The oxygen delivery apparatus disclosed herein includes oxygen cannula tubing that connects to an oxygen supply such as an oxygen concentrator and then splits off into two cannula tubes which connects to an oxygen inlet of the frame. In one example, the frame oxygen inlet is located at the tip end of each of the temples of an eyeglass frame. A hollow channel formed in each temple is in fluid communication with the frame oxygen inlet such that oxygen is flowable through the hollow channel of each respective temple to a respective hollow channel defined by the bridge portion of the frame, to a respective frame oxygen outlet at the front of the frame, preferably located in the nose pad of the eyeglass frame. Each frame oxygen outlet is connected to a nasal prong including a prong outlet, such that oxygen is flowable via the frame oxygen inlet through the eyeglass frame to exit from the prong outlet. When the eyeglass frame is positioned on a user's face, the nasal prongs are positioned into the user's nostrils to deliver oxygen to the user. In one example, the temples are integral with the lens housing, and the hollow channel through which oxygen flows is routed through a temple joint and through a portion of the lens housing such that the hollow channel is continuous from the frame oxygen inlet at the tip end of each temple to the frame oxygen outlet of the nose pad. In one example, the nasal prongs are integral to the lens housing such that the hollow channel is continuous through the lens housing and the nasal prongs. Each temple is connected to the lens housing via a temple joint. In one example, the frame is a monolithic structure, such that the temples are formed integrally with the bridge portion as a single element, and such that the hollow channel is formed within the monolithic frame as a continuous channel routed uninterrupted through the temple joint, terminating at a first channel end at the frame oxygen inlet at the temple tip and at a second channel end at the frame oxygen outlet in the frame nose pad. In another example, the temple joint includes a hinged joint which includes a fastener to fasten the temple to the bridge end of the bridge portion, and which includes sealing interfaces to connect the hollow channel of the temple with the hollow channel of the lens housing when the temple is unfolded away from the lens housing, for example, when the eyeglass frame is worn by the user. In another example, the frame is provided without temples, and the frame oxygen inlets are located at the bridge ends of a bridge portion of the frame for direct connection of the cannula tubing thereto.

One or more methods can be used to form the frame as an integral unit, e.g., as a monolithic structure, and/or to form the temples and bridge portion separately, for assembly into the hinged frame. The methods can include one or more of molding, additive manufacturing, casting, laser cutting, laser drilling, CNC machining, die cutting, and combinations thereof. In one example, the lens housing and/or the temples can be formed from multiple components which are joined, for example, by an adhesive, by welding, etc. The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

FIG. 3 is a schematic sectional view of section 3-3 of the eyeglass frame of FIG. 2 showing the hollow channel formed in the temple and in fluid communication with the frame oxygen inlet;

FIG. 4 is a schematic perspective sectional view of section 4-4 of the eyeglass frame of FIG. 1 showing the hollow channel formed in the bridge portion and nasal prong;

FIG. 5 is a schematic perspective sectional view of section 5-5 of the eyeglass frame of FIG. 1 showing the hollow channel formed in the bridge portion and temple, where the hollow channel is routed through the bridge portion to the nose pad of the frame, and through the temple joint connecting the temple and bridge portion;

DETAILED DESCRIPTION

Figure 1:
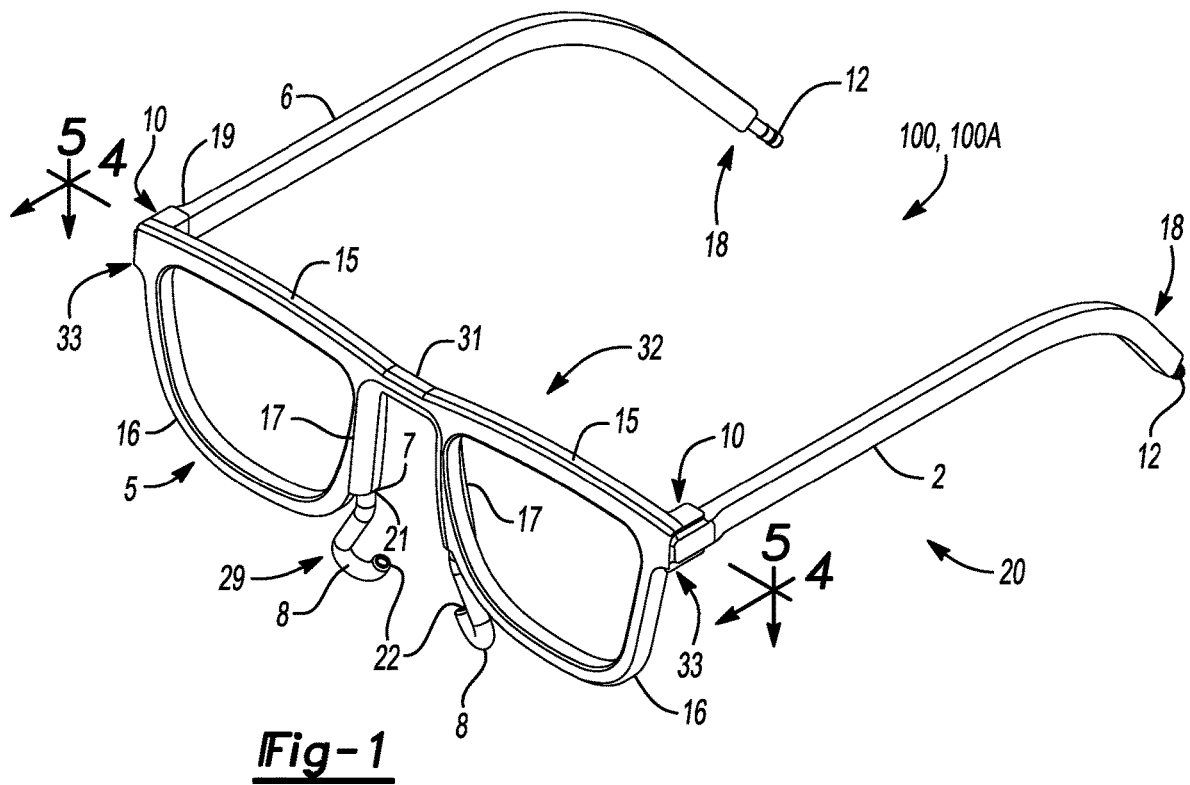
FIG. 1 is a schematic perspective front view of an oxygen delivery apparatus comprising a monolithic eyeglass frame including a bridge portion, a lens housing and a pair of integral temples. Hollow channels formed in the eyeglass frame allow gaseous oxygen to flow through the eyeglass frame from frame oxygen inlets formed at the tip ends of the temples through the frame to frame oxygen outlets located in the nose pads of the frame, and to a user via nasal prongs connected to the frame oxygen outlets. An oxygen supply tube can be connected to a frame oxygen inlet at the tip end of the eyeglass frame temples to supply oxygen to the frame.

Referring to the drawings wherein like reference numbers represent like components throughout the several figures, the elements shown in FIGS. 1-19 are not to scale or proportion. Accordingly, the particular dimensions and applications provided in the drawings presented herein are not to be considered limiting. Referring now to FIGS. 1-10 in more detail, shown is a non-limiting example of an oxygen delivery apparatus generally indicated at 100, comprising a frame 20 which can be worn by a user to deliver oxygen to the user via hollow channels 9 formed in the frame 20 and nasal prongs 8 attached to the frame 20. The user can also be referred to herein as the wearer of the oxygen delivery apparatus 100. In a non-limiting example of an oxygen delivery apparatus 100, 100A shown in FIGS. 1-8, the frame 20 can be configured as an eyeglass frame including a bridge portion 32, a lens housing 5, a left eyeglass temple 2, and a right eyeglass temple 6. In the example shown in FIGS. 1-8, the frame 20 including the bridge portion 32, the lens housing 5 and the temples 2, 6 is formed as a monolithic structure, as described in further detail herein, and such that the left and right temples 2, 6 are integral to the bridge portion 32. The nasal prongs 8 can be integrated in the monolithic structure of the frame 20 or can be selectively connected to the frame 20 such that the nasal prongs 8 are detachable, for example, for replacement and/or cleaning.

Figure 11:
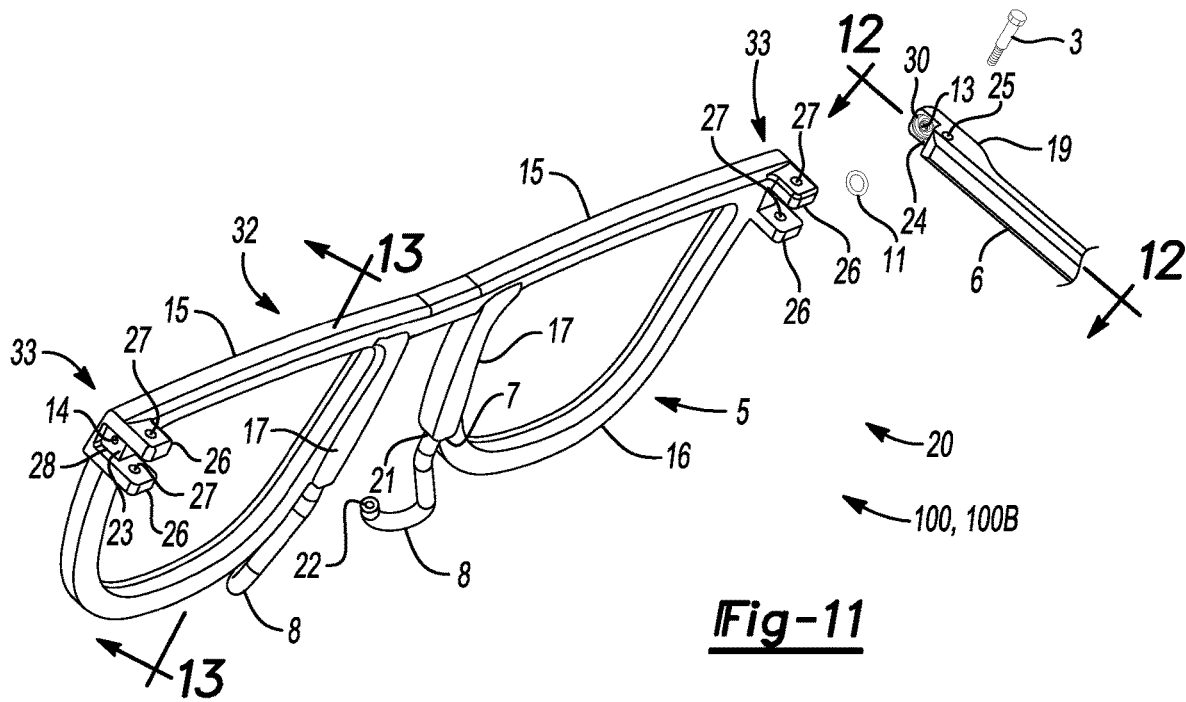
FIG. 11 is a schematic rear perspective exploded view of an oxygen delivery apparatus including an eyeglass frame including a bridge portion and a pair of detachable temples, wherein an oxygen supply tube is connected to an oxygen inlet at the tip end of the temples and hollow channels formed in the lens housing and the detachable temples. The eyeglass frame includes a temple joint configured as a hinged joint for connecting the temple to the lens housing. The temple joint includes a seal and temple and bridge sealing interfaces for selectively sealing the temple to the housing at the joint.
Figure 12:
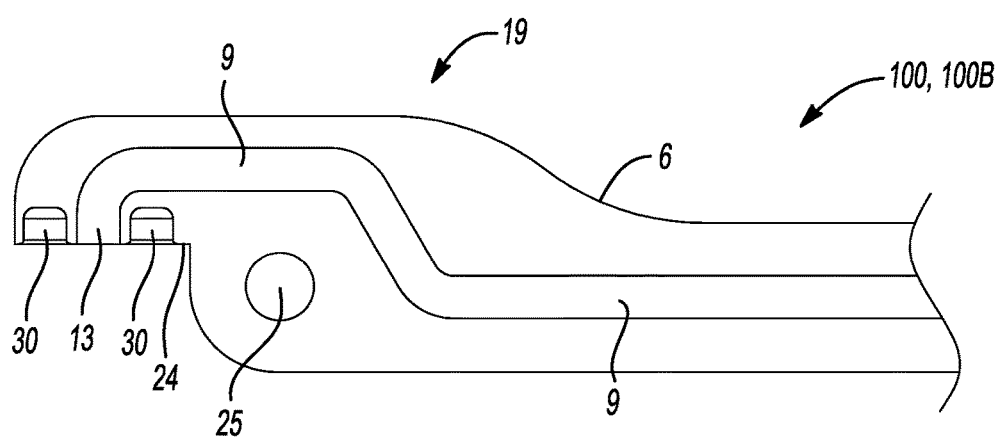
FIG. 12 is a schematic sectional top view of section 12-12 of the eyeglass temple of FIG. 11 showing the hollow channel routed around the hinged joint and through the temple.
Figure 13:
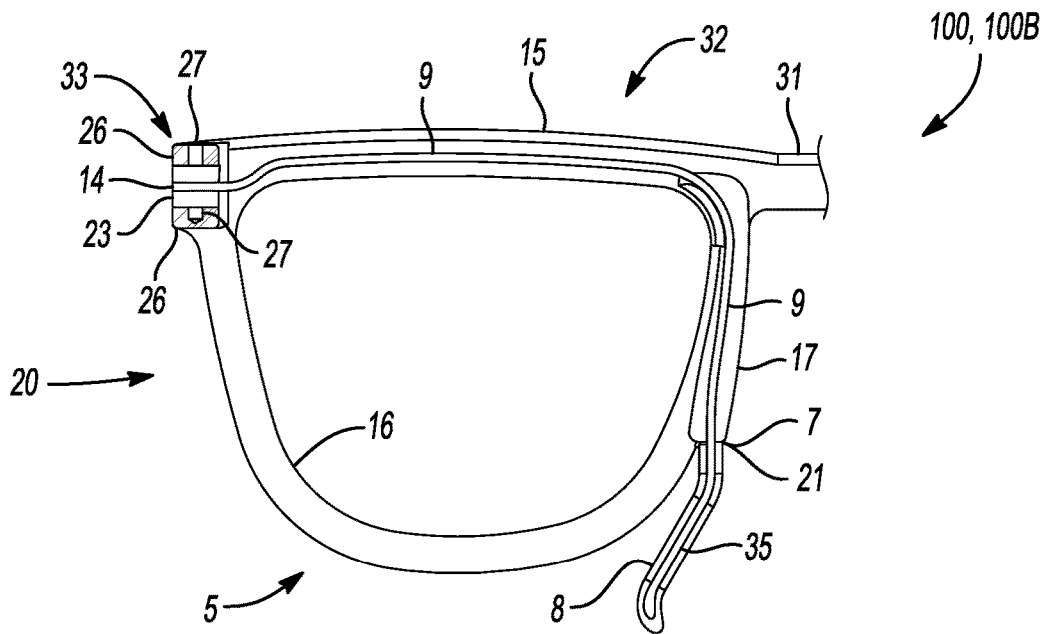
FIG. 13 is a schematic sectional rear view of section 13-13 of the eyeglass lens housing of FIG. 11 showing the hollow channel routed from the temple joint through the bridge portion, nose pads, and nasal prongs.
Figure 14:
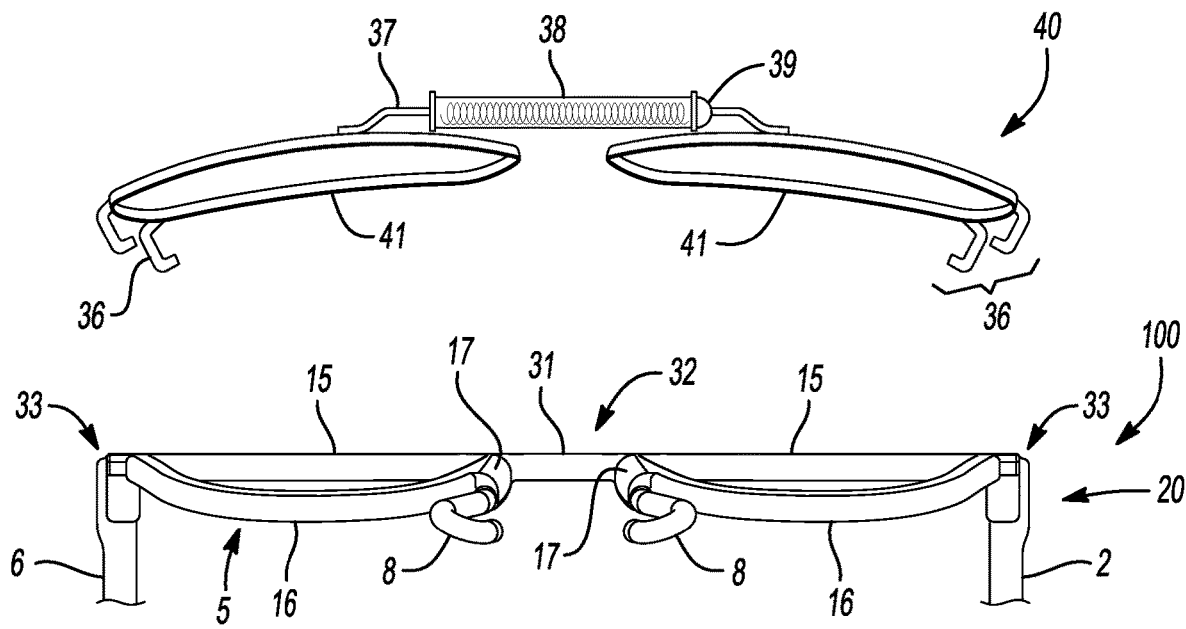
FIG. 14 is schematic bottom view of detachable lenses which utilize a spring based clip-on apparatus to attach the detachable lenses to the eyeglass frame of FIG. 1.
Figure 15:
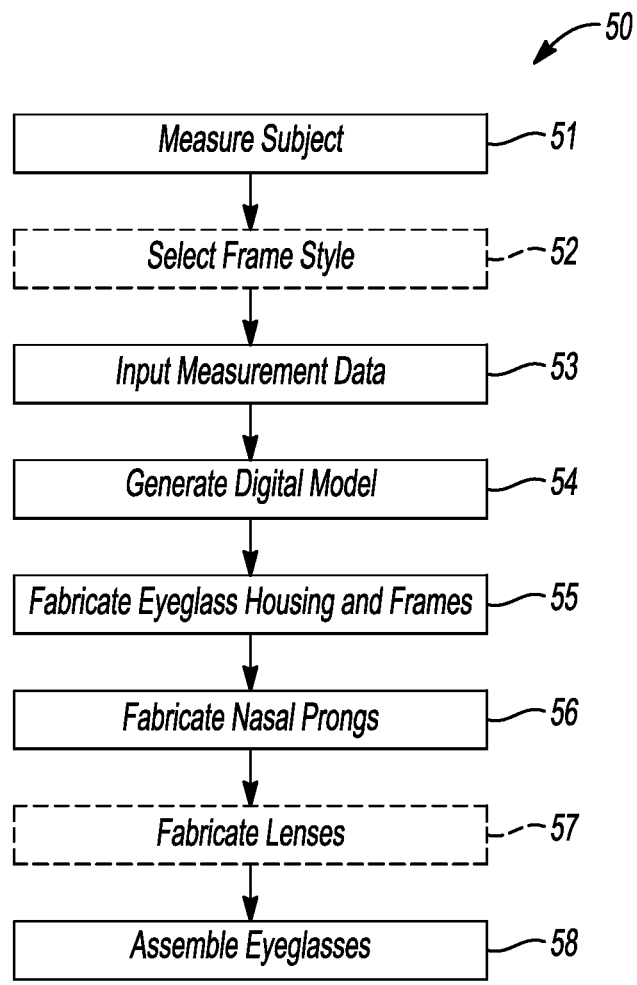
FIG. 15 is a flowchart illustrating an exemplary method for fabricating the eyeglass frame of FIG. 1.
Figure 16:
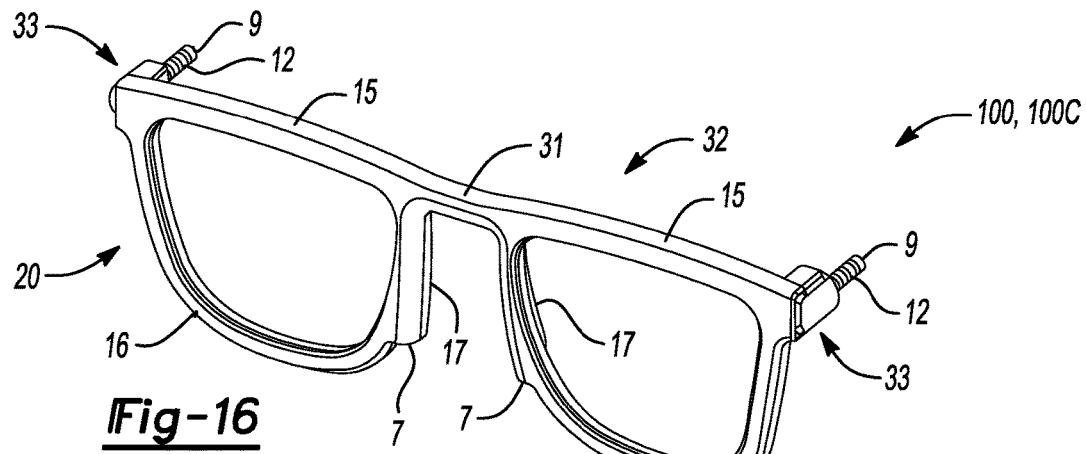
FIG. 16 is a schematic perspective front view of an example oxygen delivery apparatus including an eyeglass frame including a bridge portion having hollow channels formed therein and including frame oxygen inlets, wherein an oxygen supply tube can be connected to each frame oxygen inlet to flow oxygen through the eyeglass frame to a user via nasal prongs connected to the frame oxygen outlets of the eyeglass frame.
Figure 17:
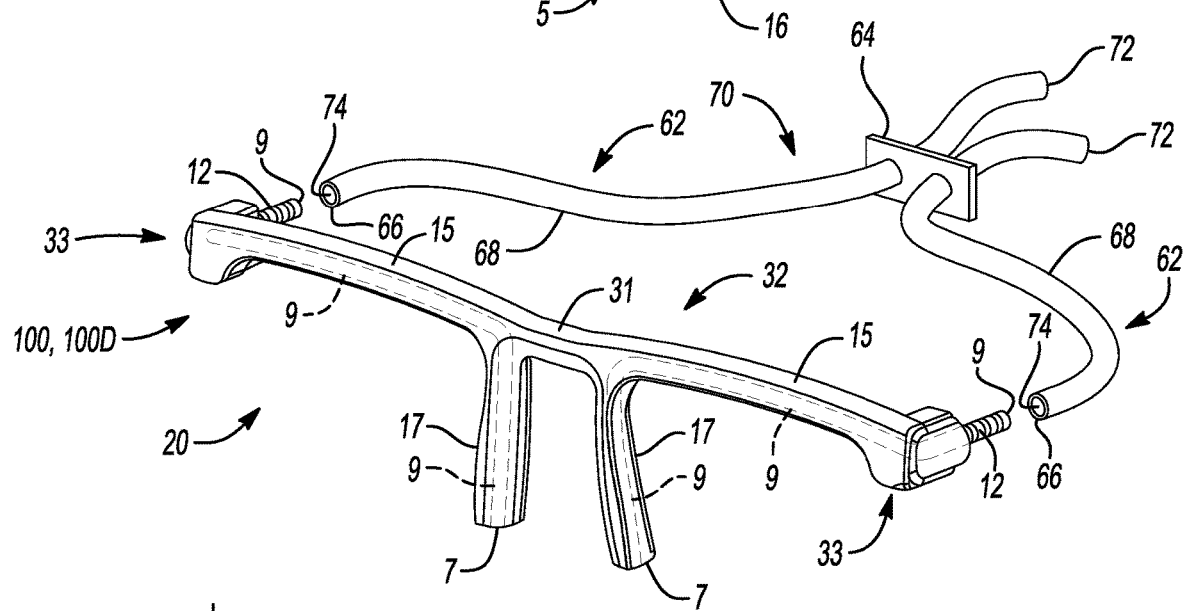
FIG. 17 is a schematic perspective front view of an example oxygen delivery apparatus including a wearable frame including a bridge portion and nose pads, the wearable frame having hollow channels formed therein and including a pair of frame oxygen inlets, wherein a cannula tubing assembly is connectable to the oxygen inlets to flow oxygen through the frame to a user via nasal prongs connected to the frame oxygen outlets located in the nose pads of the frame.
Figure 18:
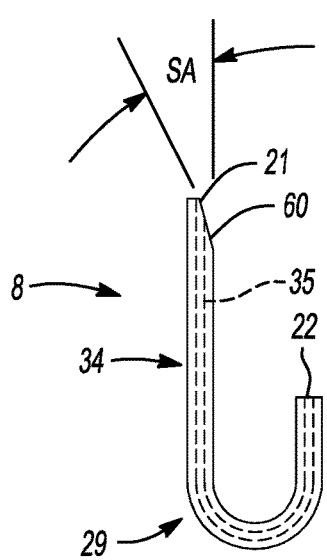
FIG. 18 is a schematic front view of an example nasal prong including a prong inlet, wherein the prong inlet includes a tapered slot.
Figure 19:
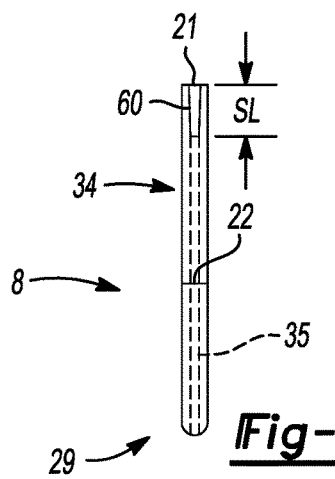
FIG. 19 is a schematic side view of the nasal prong of FIG. 18.

Cannula tubing 62 (see FIG. 17) can be attached to the frame oxygen supply inlets 12, through which oxygen can be provided to the hollow channels 9 formed in the frame 20 (see FIGS. 3-7), such that oxygen can be flowed through the frame 20 and through the nasal prongs 8 to supply oxygen to the nasal cavities of a user wearing the frame 20. FIGS. 11-13 show another non-limiting example of an oxygen delivery apparatus 100, 100B including detachable temples 2, 6 which are attached to the bridge portion 32 of frame 20 at a temple joint 10. The temple joint 10, in the example shown, is configured as a hinged joint for connecting the temples 2, 6 to the bridge portion 32, and further includes a seal 11 and defines sealing interfaces 23, 24 for selectively sealing the temple 2, 6 to the bridge portion 32 at the joint 10. FIG. 14 describes clip-on lenses which can be selectively attached to the frame 20. FIG. 15 describes an example method 50 for fabricating the oxygen delivery apparatus 100 shown in FIGS. 1-14 and 16-19. FIG. 16 shows another non-limiting example of an oxygen delivery apparatus 100, 100C including a frame 20 including an eyeglass lens housing 5 and a bridge portion 32 having hollow channels 9 formed therein in fluid communication with frame oxygen inlets 12 formed on the bridge ends 33, wherein an oxygen supply tube, also referred to herein as cannula tubing 62, can be connected to the frame oxygen inlet 12 to flow oxygen through the frame 20 to a user via nasal prongs 8 (see FIG. 18) connected to the nose pads 17 of the bridge portion 32. FIG. 17 shows another non-limiting example of an oxygen delivery apparatus 100, 100D including a frame 20 including a bridge portion 32, the frame 20 having hollow channels 9 formed therein and including a pair of frame oxygen inlets 12, wherein a cannula tubing assembly 70 is connectable to the frame oxygen inlets 12 to flow oxygen through the frame 20 to a user via nasal prongs 8 connected to the nose pads 17 of the frame 20. When not referring to a particular example, the oxygen delivery apparatus 100, 100A, 100B, 100C, 100D can be collectively referred to herein as the oxygen delivery apparatus 100. FIGS. 18 and 19 show a non-limiting example of a nasal prong 8 including a prong inlet 21, wherein the prong inlet 21 includes a linear portion and a tapered slot 60, where the slot can be closed or collapsed during insertion of the prong inlet 21 into the frame oxygen outlet 7, to ease attachment of the prong 8 to the frame 20.

Referring now to the oxygen delivery apparatus 100 in more detail, FIG. 1 shows the principle of the oxygen delivery apparatus 100, where oxygen supply cannula tubing 62 (see FIG. 17) through which oxygen flows from an oxygen supply (not shown) can be connected to the frame oxygen inlets 12 at the tip ends 18 of the temples 2, 6 of the frame 20. Frame 20 is configured in the example apparatus 100A shown in FIG. 1 as a monolithic eyeglass frame 20. The eyeglass frame 20 includes one or more hollow channels 9 to receive oxygen from the cannula tubing 62, and to convey the oxygen through the eyeglass frame 20 to output the oxygen from the eyeglass frame 20 via prong outlets 22 defined by nasal prongs 8. In use, the prong outlets 22 of the nasal prongs 8 are positioned within the nostrils of a user wearing the eyeglass frame 20, such that oxygen is conveyed from the oxygen supply via the cannula tubing 62 and hollow channels 9 of the frame 20, and is outputted via the prong outlets 22 into the nostrils of the user. An oxygen supply cannula tubing assembly 70, such as shown in FIG. 17, includes a pair of cannula tubes 62 each having a tubing oxygen outlet 66 which can be connected respectively to each of the left eyeglass temple 2 and the right eyeglass temple 6, where the two cannula tubes 62 may be joined in a y-shaped connection to a single tubular member (not shown) which can be connected to the oxygen supply such as an oxygen concentrator or a pressurized oxygen tank, such that oxygen can be flowed through the tubing channels 74 of the cannula tubing 62. The configuration shown in FIG. 1 is non-limiting, for example, the oxygen delivery apparatus 100 can be configured and/or operational with an oxygen supply connected via cannula tubing 62 to only one of the two temples 2, 6 connected via hollow channels 9 to at least one of the two nasal prongs 8. In some embodiments of the oxygen delivery apparatus 100, the frame oxygen inlet 12 may be configured as a nipple or tubular extension having grooves or barbs formed on the exterior surface thereof, as shown in FIGS. 3 and 12, to connect tubing oxygen outlets 66 of the oxygen supply cannula tubing 62 to the frame oxygen inlets 12. Similarly, the frame oxygen outlet 7 may be configured as a barbed or grooved tubular extension to attach the nasal prongs 8, where the barbed or grooved configuration further increases the sealing effectiveness and prevents the oxygen supply cannula tubing 62 and/or the prongs 8 from slipping off, which would be highly inconvenient for the user.

Figure 6:
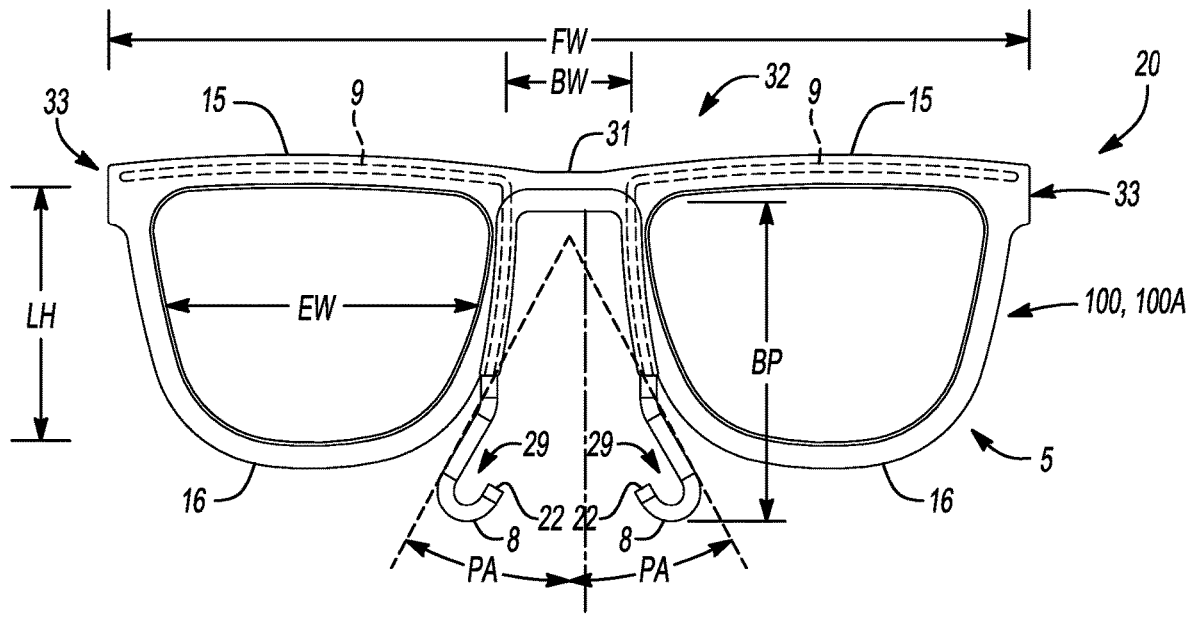
FIG. 6 is a schematic front view of the eyeglass frame of FIG. 1 showing nasal prongs attached to the frame oxygen outlets.
Figure 7:
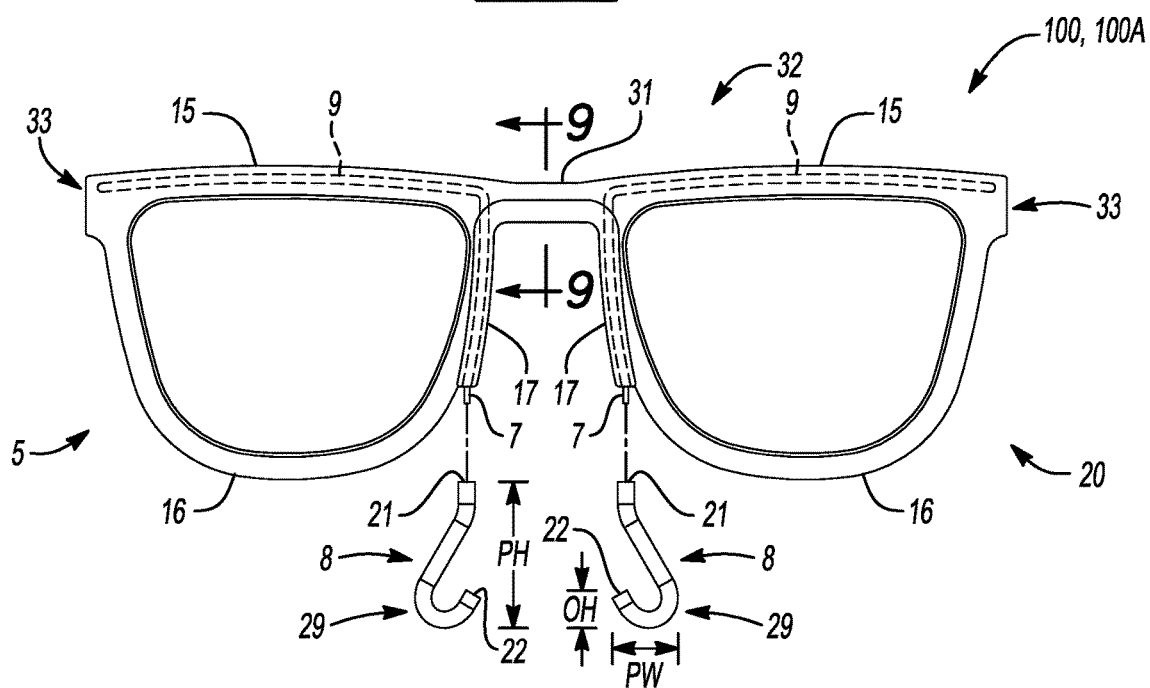
FIG. 7 is a schematic front view of the lens housing of the eyeglass frame of FIG. 1 showing the nasal prongs detached from the frame oxygen outlets.

Due to the pressure-differential between the hollow channels 9 and the tubing channels 74 of the oxygen supply cannula tubing 62, the higher-pressure incoming oxygen gas will tend to pass through the narrow passage of the hollow channels 9 inside the bridge portion 32 of the eyeglass frame 20, into the region of lower pressure, e.g., the prong outlet 22, hence allowing the oxygen to flow through the temples 2, 6 and the bridge portion 32 via a frame outlet 7 into the hollow prong channels 35 of the nasal prongs 8 and to be delivered to the user via the prong outlets 22 of the nasal prongs 8. FIGS. 6 and 7 show a front view of the frame 20, including a bridge portion 32 including nose pads 17, and a lens housing 5 including rims 16 for retaining eyeglass lenses (not shown) in the frame 20. FIGS. 4-7 show the internal hollow channels 9 which are routed around the contours of the bridge portion 32 including nose pads 17, in fluid communication with the frame oxygen outlets 7, which in the example shown are positioned in the nose pads 17. Nasal prongs 8 connected at the prong inlets 21 to the frame 20 allow delivery of oxygen to the user by flowing oxygen via the prong channels 35 (see FIG. 18) of the prong outlets 22 into or around the nostril region of the user. Each nasal prong 8 can be formed integrally with the frame 20 (see FIGS. 4 and 6), or can be attached via the frame oxygen outlet 7 (see FIGS. 7 and 17-19) where a prong oxygen inlet 21 of the nasal prong 8 is selectively attachable to the lens frame oxygen outlet 7 to attach the nasal prong 8 to the nose pad 17 of the lens housing 5. The nasal prong 8 can be attached to the prong oxygen inlet 21 by friction fit, using a mechanical locking mechanism, using a threaded connection, etc. In a non-limiting example, the frame oxygen outlet 7 is configured as a nipple or tubular extension, as shown in FIG. 7, which can have grooves or barbs formed on the exterior surface, such that the prong 8 can be attached to the frame oxygen outlet 7 by inserting the tubular frame oxygen outlet 7 into the prong channel 35 of the prong 8.

In a non-limiting example, the frame oxygen outlet 7 is recessed in the nose pad 17 (see FIG. 16) such that the prong inlet 21 can be inserted into the hollow channel 9 of the nose pad 17 to retain the prong inlet 21 in fluid communication with the frame outlet 7. The aesthetics of this embodiment of the eyeglass frame 20, wherein the frame oxygen outlets 7 are recessed inside the nose pads 17, is advantaged in that the frame oxygen outlets 7 do not protrude from the nose pads 17 and do not affect the exterior appearance of the frame 20. In this example where the prong inlet 21 is attached by insertion directly into the hollow channel 9 at the frame oxygen outlet 7, the apparatus 100 is advantaged that with the nasal prongs 8 detached, the eyeglass frame 20 aesthetically appears to be a normal (unmodified) pair of eyeglasses, wearable by the user as normal eyeglasses even at times when oxygen therapy is not required.

In one example, the prong oxygen inlet 21 can be tubular and have a barbed or grooved exterior surface, similar to the configuration of the frame oxygen inlet 12 shown in FIG. 3, such that the prong oxygen inlet 21 can be inserted into the hollow channel 9 of the frame 20 via the frame oxygen outlet 7, to retain the nasal prong 8 to nose pad 17. In a non-limiting example, the prong inlet 21 can include a vee-slot 60, also referred to herein as a tapered slot, as shown in FIGS. 18 and 19. In this example, during attachment of the nasal prong 8 to the frame 20, the tapered slot 60 can be compressed to close the slot 60, thereby decreasing the outer diameter of the nasal prong 8 at the prong inlet 21, to facilitate insertion of the prong inlet 21 into the frame oxygen outlet 7 and hollow channel 9 of the frame 20. After insertion of the collapsed prong inlet 21 into the frame oxygen outlet 7, compression of the tapered slot 60 is released, such that the tapered slot 60 reopens to form a friction fit between the prong inlet 21 and the frame outlet 7, to retain the prong 8 in the hollow channel 9 of the nose pad 17, and such that the hollow channel 9 is in fluid communication with the prong channel 35. The example of a tapered slot 60 shaped as a vee-shaped slot is non-limiting. For example, the tapered slot 60 could be shaped as a rectangular slot, a U-shaped slot, an asymmetrical slot, or other configuration such that the tapered slot 60 is compressible to close the slot 60 to decrease the outer diameter of the nasal prong 8 at the prong inlet 21 during insertion of the prong inlet 21 into the frame oxygen outlet 7.

Figure 8:
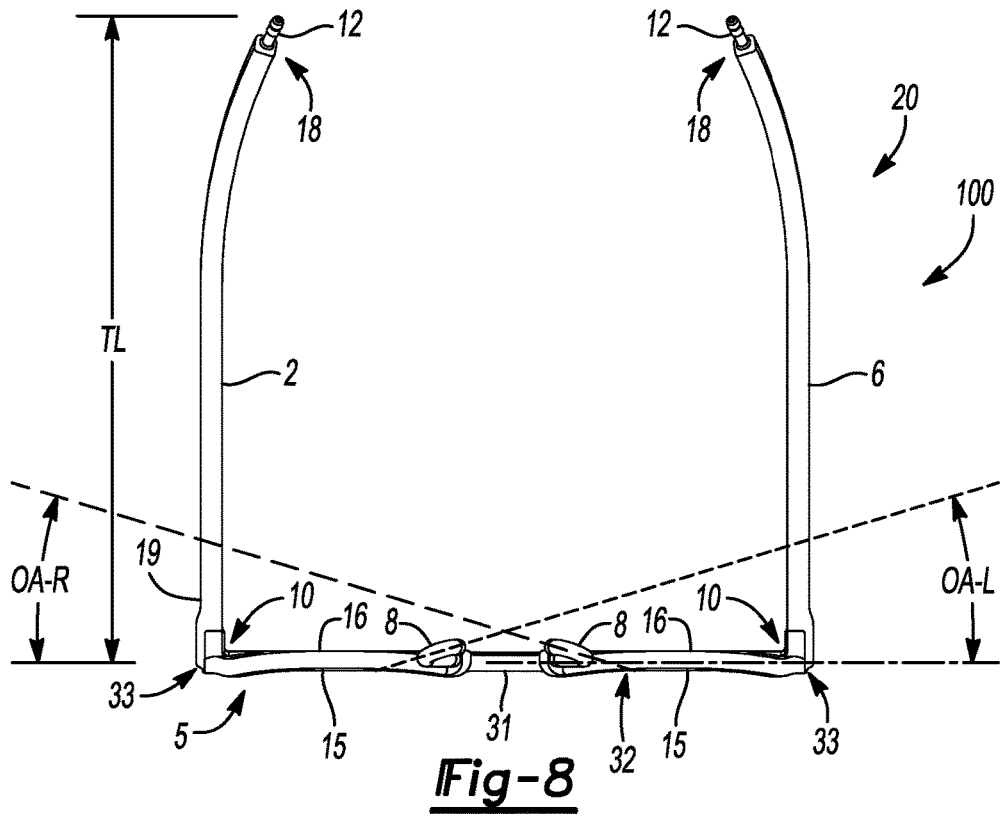
FIG. 8 is a schematic bottom view of the eyeglass frame of FIG. 1, showing the nasal prongs oriented such that the prong outlet is posterior of the bridge portion and is characterized by a posterior outlet angle relative to the bridge bar of the eyeglass frame.
Figure 9:
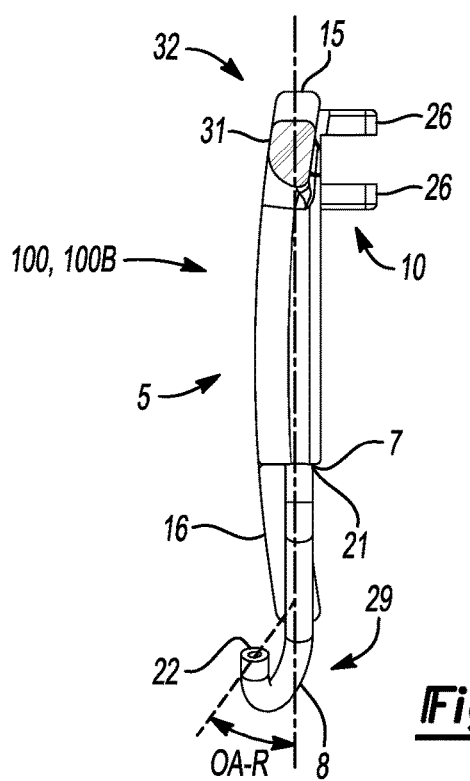
FIG. 9 is a schematic sectional view of section 9-9 of the eyeglass frame of FIG. 7 showing the eyeglass frame with a nasal prong having an anterior outlet angle.
Figure 10:
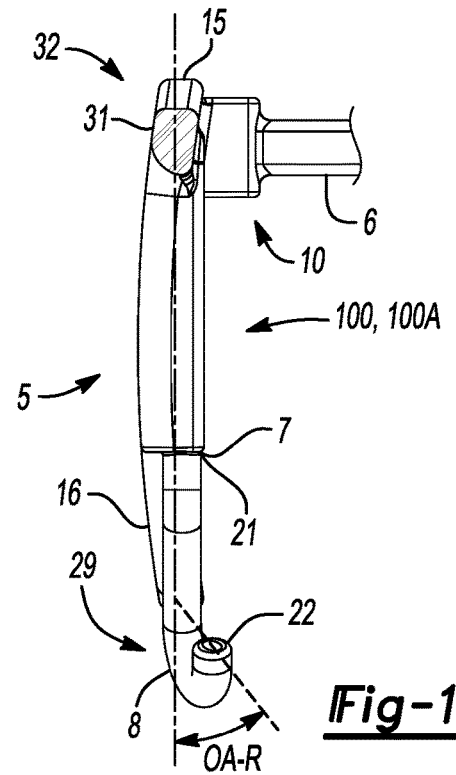
FIG. 10 is a schematic sectional view of section 9-9 of the eyeglass frame of FIG. 7 showing the eyeglass frame with a nasal prong having a posterior outlet angle.

In one example, the nasal prong 8 is rotatable adjustable relative to bridge portion 32, to adjust the outlet angle (OA) relative to the bridge bar 15, as shown in the examples illustrated by FIGS. 8-10, for the comfort of the user and/or positioning of the prong outlet 22 in the user's nasal cavity for effective oxygen therapy. In one example, the nasal prongs 8 can be removed and/or reinstalled, for example, during cleaning and/or periodic replacement of the nasal prongs 8. In one example, the nasal prongs 8 can be configured, e.g., by shape, material, or otherwise, as disposable nasal prongs 8 which are periodically replaced by the user. In one example, the nasal prongs 8 can be selected from a variety of shapes, sizes, prong angles (PA), contour shape 29, and/or colors to accommodate differences in nose shape, size, complexion, etc.

Figure 2:
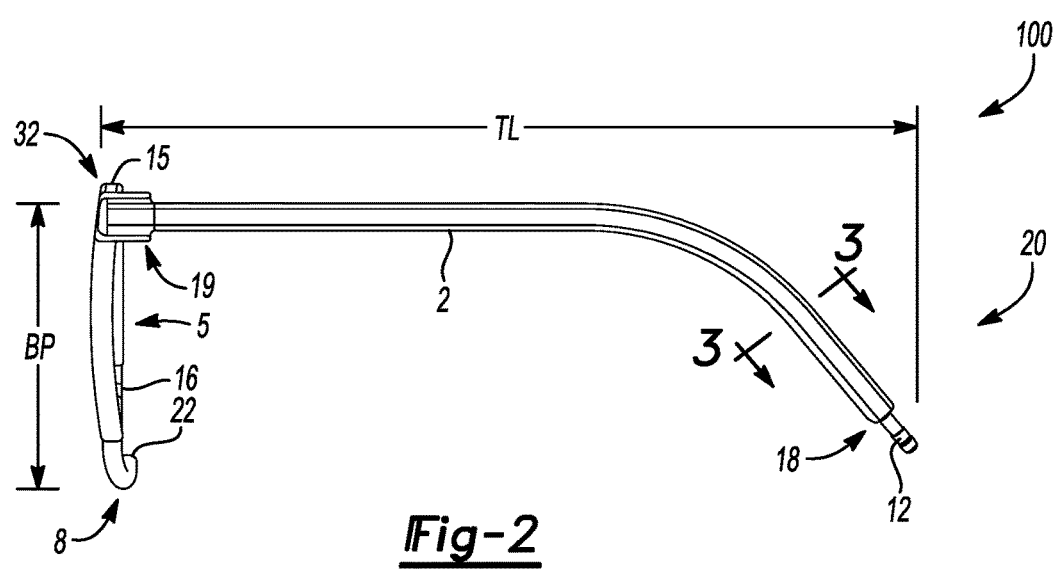
FIG. 2 is a is a schematic side view of the eyeglass frame of FIG. 1.

Referring to FIGS. 1-3, each of the temples 2, 6 includes a tip end 18 and a joint end 19. The temple 2, 6 is attached to the bridge portion 32 at the temple joint 10, as described further herein. The bridge portion 32 includes a bridge bar 15 which extends along the top of the bridge portion 32 and includes a nose bridge 31, also referred to herein as a bridge 31. A lens housing 5 can be attached to or integrally formed with the bridge portion 32, and can include rim portion 16, which can also be referred to herein as rims or rim wires, which, in combination with the bridge bars 15, are configured to retain lenses (not shown) in the frame 20. The lenses can be, for example, prescription lenses, non-prescription lenses, tinted lenses, standardized lenses such as the lenses used in reading glasses available over the counter, or clear lenses, for example, in situations where a user does not require corrective lenses however it is desirable that the oxygen delivery apparatus 100 provide the appearance of conventional spectacles or eyeglasses. The examples are non-limiting, and it would be understood that the eyeglass frame 20 could be provided to the user with no lenses, for use by the user as an oxygen delivery apparatus 100. In one example, the oxygen delivery apparatus 100 can include detachable lenses which can be selectively inserted into the lens housing 5 at the user's option. Furthermore, these lenses could be prescription, wherein the detachable single vision, progressive, and/or bifocal lenses could be customized based on the user's prescription and installed into grooves inside the lens housing 5 by an optical lens manufacturing facility, optician, optical shop, and/or ophthalmologist, either as part of the method 50 of making the oxygen delivery apparatus 100 or afterwards the user has obtained the oxygen delivery apparatus, where installation of the lenses can be performed by a separate company or individual at the discretion of the user. This lens prescription data could be uploaded as an electronic copy or file by an ophthalmologist or entered manually as number values by the user. These numerical values could include single or dual pupillary distance (PD), spherical correction (SPH), cylindrical correction (CYL), axis correction (AXS), PRISM values, Near-Vision (NV-ADD), and/or type of progressive lens. In one example, the detachable lenses could be tinted for attachment to the lens housing 5 to provide the user with sunglasses. For example, the detachable lenses could be configured as magnifying lenses for insertion into the lens housing 5 by the user when reading or performing detail work.

In a non-limiting example, a detachable lens assembly 40 including lenses 41 can be configured to clip-on to the frame 20, as shown in FIG. 14, wherein a spring based clip-on mechanism 37 can be used to adjust the length and/or width dimensions of the clip attachments using clips 36 attached to the lenses 41 to attach the detachable lens assembly 40 to the frame 20. The example clip-on mechanism 37 shown in FIG. 14 utilizes a spring 38 inside a spring housing 39 to adjust the width of the lens assembly 40 to the eyeglass frame 20, depending on factors such as size of the person's face and/or facial features, which could influence the size of the eyeglass frame 20 if customized based on digital measurements and/or a computerized model as described for FIG. 15. This could be particularly useful, for example, where the eyeglass frames are fabricated using additive manufacturing technology, based on a computer model or measurement of the person's facial features, since the clip-on lens assembly 40 could allow for the use of lenses 41 of standardized lens sizes in the lens assembly 40, and provide the user the advantage of conveniently and easily changing between different types of lenses 41, such as reading lenses, sunglasses lenses, and/or prescription lenses for vision correction. In another example, the clip-on lens assembly 40 could be configured to include a hinge-based mechanism to attach to the lens assembly 40 to the nose bridge 31 of the bridge portion 32 of the frame 20.

As shown in the Figures, the joint end 19 of each of the temples 2, 6 is connected to the lens housing 5 at a temple joint 10. As illustrated by FIGS. 1-13, a hollow channel 9 extends from the frame oxygen inlet 12 through the temple 2, 6, through the temple joint, through the bridge bar 15 and through the nose pad 17, to the frame oxygen outlet 7. Oxygen exiting the frame oxygen outlet 7 flows via a prong inlet 21 through a hollow prong channel 35 of a nasal prong 8 attached to the frame oxygen outlet 7 at the nose pad 17, and exits the nasal prong 8 via a prong outlet 22. In use, the prong outlet 22 is positioned in or immediately adjacent to the nostril of the wearer of the frame 20, to deliver oxygen to the wearer. In the example shown, the frame 20 includes left and right hollow channels 9, each extending through a respective left and right temple 2, 6 and through a respective left and right bridge bar 15 to flow oxygen from the frame oxygen inlets 12 to the frame oxygen outlets 7 of the respective left and right nose pads 17 and nasal prongs 8 attached thereto. The example of left and right hollow channels 9 is non-limiting. For example, an oxygen delivery apparatus 100 can be configured including only a left hollow channel 9 or a right hollow channel 9. Further, the example routing of the hollow channels 9 through the bridge portion 32 is non-limiting. For example, the hollow channel 9 can be routed through lens housing 5 including the rim portion 16 to the frame oxygen outlet 7. Further, the example configuration of the frame oxygen outlet 7 located in and/or extending from the nose pad 17 is non-limiting. For example, a frame oxygen outlet 7 can be located along the rim portion 16 in fluid communication with a hollow channel 9 formed in the rim portion 16, and the nasal prong 8 can be attached thereto.

When the frame 20 is in use, e.g., is worn by a user, the nose bridge 31 and the nose pads 17 rest, respectively, on the bridge and sides of the user's nose, and the temples 2,6 extend over the user's ears such that the eyeglass frame 20 is supported by and retained on the user's face and head, and such that the prong outlets 22 of the nasal prongs 8 are positioned within the user's nostrils. The nose pads 17 in the non-limiting examples shown in the figures are integral to the bridge portion 32. The nose pads 17 can further include an attachable element (not shown) which may be attached to the nose pad 17, for example, by an adhesive or screw attachment, to adjust the fit of the eyeglass frame 20 to a particular user. Further, to optimize comfort of the user, the oxygen delivery apparatus 100, including the bridge portion 32, the lens housing 5, the temples 2, 6 and/or the nasal prongs 8 can be sized based on the size and shape of the individual user's head and the size, shape and position of the individual user's eyes, ears, and nose on the individual user's head, e.g., the size, shape and position of the individual user's facial features. In one example, the temples 2, 6, the bridge portion 32 including the nose pads 17, the lens housing 5, and/or the nasal prongs 8 can be fabricated in standardized, e.g., incremental sizes and shapes and made available for combination, e.g., assembly into a frame 20 sized to measurements taken of the individual user's head and facial features. In another example, referring to the method shown in FIG. 15 and described in further detail herein, the user's head and facial features can be measured and/or digitized, and a model of the frame 20, with or without the nasal prongs 8, can be generated based on the user's measurements, from which an oxygen delivery apparatus 100 can be fabricated, for example, using additive manufacturing, to provide an oxygen delivery apparatus 100 including a frame 20 and/or nasal prongs 8 which are customized to the individual user's head and facial features. By fabricating a customized oxygen delivery apparatus 100 fitted to the particular user, the wearing comfort of the apparatus 100, and the effectiveness of the apparatus 100 to direct oxygen flow into the user's nostrils, is optimized. As such, the user's compliance with an oxygen therapy regimen is likely to be significantly higher than the user's compliance when using a traditional cannula-based apparatus, due to the increased comfort, favorable aesthetic appearance of the frame 20, and effectiveness in directing the oxygen flow.

Referring to FIGS. 2 and 6-8, shown are various dimensions which can be included in the process of measuring the user, generating the model, and/or fabricating the eyeglass frame 20, including the bridge portion 32, lens housing 5, temples 2, 6, and/or nasal prongs 8. The examples provided are non-limiting, and it would be understood that additional and/or other dimensions of the oxygen delivery apparatus 100 and/or the user's head, ears, eyes, nose, or other facial features can be incorporated into the method 50 described herein (see FIG. 15) for fabricating the oxygen delivery apparatus 100. By way of non-limiting example, the method 50 can include generating a comprehensive digital model of the user's head, from which data and measurements can be obtained to generate a digital model of an oxygen delivery apparatus 100 customized to the user's physical attributes and oxygen therapy requirements. Further, the digital model of the oxygen delivery apparatus 100 can incorporate the user's preferences as to style, shape, size, color, etc. of the frame 20, and/or the user's requirements as to lens shape, size, etc. as required for aesthetics or corrective prescription, such that the aesthetic and corrective lens characteristics of the eyeglass frame 20 can also be customized. As such, the bridge portion 32, the lens housing 5 and/or the eyeglass temples 2, 6 may have a different aesthetic design than what is shown in figures. Non-limiting examples of measurements, dimensions and/or characteristics which can be included individually and/or in combination in the modeling of the user's head and facial characteristics, and/or the modeling of the oxygen delivery apparatus 100 including a frame 20 and nasal prongs 8 include, as shown in FIGS. 2 and 6-8, a temple length (TL), a bridge to prong height (BP), a frame width (FW), an eye width (EW), a lens height (LH), a bridge width (BW), a prong angle (PA), a prong outlet angle (OA), a prong height (PH), a prong width (PW), and a prong outlet height (OH).

Measurements of the user's head and/or facial features which correspond to one or more of these measurements, dimensions and/or characteristics can be included in the modeling method 50 disclosed herein. For example, measurements of the user's nose, including the width of the bridge, the length of the nose, the bialar angle, the interalar distance, etc., can be inputted to model the oxygen delivery apparatus 100 to be fabricated for that user using the method 50 described herein, to optimize, for example, the configuration, size and shape of the bridge bars 15, bridge 31, nose pads 17, and nasal prongs 8 for the user's comfort and effectiveness of the oxygen therapy. As shown in FIGS. 6-10, in one example, the nasal prongs 8 can include a generally J-shaped portion extending at a prong angle (PA) from the center of the bridge 31, and including a contoured portion 29, where the prong angle (PA), the outlet angle (OA), the shape of the contoured portion 29 including the prong width (PW) and the outlet height (OH) in combination determine the fit and comfort of the nasal prongs 8 as positioned in the user's nostrils when in use, e.g., when the user is wearing the eyeglass frame 20. By incorporating data based on the user's features into the digitized model from which the oxygen delivery apparatus 100 is fabricated for the user, fit of the nasal prongs 8, including clearance from the nostril and/or face to minimize contact discomfort, abrasion, etc., can be optimized. In one example, as shown in FIGS. 9 and 10, the nasal prongs 8 can be configured such that the outlet angle (OA) of the prong oxygen outlet 22 is at an outlet angle which can be either anterior or posterior relative to the bridge 31 and/or bridge bar 15, depending on the anatomical requirements of the user. In one example, the nasal prongs 8 can be rotatably attached to the frame oxygen outlet 7 such that the outlet angle (OA) is adjustable during use. By way of non-limiting example, the prong outlet 22 can be shaped as a straight tube, can be flared, curved, or otherwise optimized for the user.

In another example shown in FIGS. 18 and 19, the nasal prongs 8 can be configured such that the portion 34 of the nasal prong 8 extending from the prong inlet 21 to the contoured portion 29 is substantially straight, e.g., without any curvature or bends, such that the portion 34 can be characterized as a linear portion 34 of the nasal prong 8. When the prong 8 shown in FIGS. 18 and 19 is inserted into the frame oxygen outlet 7, and the frame 20 is worn by a user with the prong outlet 22 positioned in the wearer's nostril, the linear portion 34 of the prong 8 rests and/or presses against the nasal ala of the wearer's nose and/or between the nasal ala and the cheek of the wearer, such that the appearance of the prong 8 on the wearer's face is minimized and/or made less noticeable, thus providing a more favorable aesthetic for the wearer. In one example, the linear portions 34 of the left and right nasal prongs 8 can cooperate to exert a clamping pressure on the sides and/or ala of the wearer's nose, to stabilize the positioning of the nasal prongs 8 on the wearer's face and/or in the wearer's nostrils, and/or to stabilize the positioning of the frame 20 on the wearer's face. In one example, the prong 8 can be made of a material which is tinted or colored to match and/or blend with the complexion of the wearer, to make the presence of the nasal prong 8 on the wearer's face less noticeable.

The examples of nasal prongs 8 shown in FIGS. 6, 7, 18 and 19 are non-limiting, and it would be understood that other configurations of nasal cannula could to connected to the frame oxygen outlets 7 to flow oxygen into the wearer's nostrils. In one example, a dual prong nasal cannula, while more visually noticeable as being worn by the user, could be configured to attach to the frame oxygen outlets 7 for delivery of oxygen via the hollow channels 9 of the frame 20 to the user's nostrils. In one example, the nasal prongs 8 and/or the frame oxygen outlets 7 can be adapted such that oxygen delivery apparatus 100 can be used similar to or as a Continuous Positive Airway Pressure (CPAP) device. The nasal prongs 8 could be configured to provide a seal between the nose and the rest of the face, for example, by configuring the prong outlets 22 as nose buds to seal the nostril opening. In another illustrative example, a nasal pillow CPAP mask could be adapted for connection to the frame oxygen outlets 7.

Referring to FIGS. 1-5, in one example configuration, the eyeglass frame 20 including the bridge portion 32, lens housing 5 and temples 2, 6 can be monolithic, e.g., formed as a single structural element such that the temple joint 10 is integral to the eyeglass frame 20, and the temple 2, 6 is continuous with and extends from the bridge end 33 of the bridge bar 15, to define the temple joint 10, where the temple joint 10 is integral to the frame 20. In this embodiment, as shown in FIGS. 4-5, the hollow channel 9 is a continuous uninterrupted channel connecting the frame oxygen inlet 12 to the lens frame oxygen outlet 7, such that the entire length of the hollow channel 9 from the frame oxygen inlet 12 to the frame oxygen outlet 7 is contained within the monolithic structure of the frame 20. The continuous hollow channel 9 forming within the monolithic frame 20 shown in FIGS. 1-5 is advantaged by providing a sealed (uninterrupted and leak-proof) path for the continuous flow of oxygen from the frame oxygen inlet 12 to the frame oxygen outlet 7. In this example, the temple joint 10 may be formed such that movement of the temple 2, 6 relative to the bridge portion 32 may have limited flexibility, or may be substantially rigid and/or fixed, such that the temples 2, 6 are not foldable against the bridge portion 32. As described in further detail herein, the monolithic eyeglass frame 20 can be formed, for example, by one or more of molding, casting, and additive manufacturing.

In another example configuration shown in FIGS. 11-13, the temple joint 10 can be configured as a foldable hinged joint including a fastener 3, such as a screw 3 which can be threaded through one or more of the temple 2, 6 and the bridge end 33 and/or a pin 3 which can be pressed, riveted, or otherwise retained in the hinged temple joint 10 in order to allow the eyeglass temples 2 or 6 to folded away from and against the bridge portion 32, allowing the eyeglass temples 2, 6 to articulated via the hinged joint 10 between an open position, for example, when the eyeglass frame 20 is worn by the user and the temple 2, 6 is substantially perpendicular to the bridge portion 32, and a closed position, for example, when the temples 2, 6 are folded against and adjacent to the bridge portion 32, as when the oxygen delivery apparatus 100 is not in use. In one example, a nut or washer can be used to retain the fastener 3 in the hinged joint 10. In a non-limiting example shown in FIGS. 11-13, and referring to the hinged temple joint 10 formed by joining the right temple 6 to the right bridge end 33 of the bridge portion 32, the joint end 19 of the right temple 6 includes a temple hole 25 for receiving the fastener 3 during attachment of the temple 6 to the bridge end 33. The bridge end 33 includes opposing hinge flanges 26, each including a flange hole 27 (see FIGS. 11 and 13), for receiving the fastener 3 during attachment of the temple 6 to the bridge end 33. In one example, the fastener 3 is a screw retained in the flange and temple holes 26, 27 by a retainer such as a nut or washer. In one example, at least one of the flange and temple holes 26, 27 is a threaded hole, and threads of the fastener 3 engage the threads of the flange and/or temple holes 26, 27 to retain the temple 6 to the bridge end 33, forming a hinged joint such that the temple 6 can be folded against the bridge portion 32 in a closed position and/or folded away from the bridge portion 32 in an open position as during use.

In the non-limiting example shown, the hollow channel 9 formed in the temple 2, 6 extends from the frame oxygen inlet 12 at the temple tip 18 to a temple oxygen outlet 13 at the joint end 19 of the temple 2, 6. The temple 2, 6 includes a substantially flat temple interface surface 24 (see FIG. 12) surrounding the temple oxygen outlet 13, such that the temple oxygen outlet 13 is flush with, e.g., does not protrude from, the temple interface surface 24. A recessed groove 30 is formed around the temple oxygen outlet 13, as shown in FIGS. 11 and 12, and is configured to receive a sealing element 11 (see FIG. 11), which in the present example is configured as an O-ring or gasket conforming to the shape of the recessed groove 30. As shown in FIG. 13, the bridge end 33 includes a substantially flat bridge interface 23 surrounding a bridge oxygen inlet 14, such that the bridge oxygen inlet 14, which is in fluid communication with the hollow channel 9 formed in the bridge portion 32, is flush with, e.g., does not protrude from, the bridge interface surface 23. In the example shown, the bridge interface 23 positioned in a recess 28 (see FIG. 11) formed in the bridge portion 32 by the hinge flanges 26. The example of an O-ring is non-limiting, and other sealing elements 11 can be used. For example, a sealing element 11 such as a substantially flat gasket can be adhered to the flat surface of the bridge interface 23 and/or the temple interface 24, such that when the temple 2, 6 is folded away from the bridge portion 32 into an open position, the flat gasket 11 seals the bridge interface 23 to the temple interface 24 to prevent and/or substantially eliminate leakage of oxygen from the hollow channel 9 at the hinged temple joint 10. In one example, the sealing element 11 can be selectively replaceable, for example, in the event of wear and/or damage of the sealing element 11 during use. FIG. 12 shows a sectional view of the eyeglass temple 2, 6 that illustrates the hollow channel 9 formed in the joint end 19 of the temple 2, 6 is routed through the body of the temple 2, 6 around the temple hole 25, such that the screw 3 can be threaded or a pin 3 can be pressed through the temple hole 25 when attaching the temple 2, 6 to the bridge end 33 to form the hinged joint 10. Oxygen gas is supplied to the eyeglass temple oxygen supply inlet 12 by connecting the oxygen supply cannula tubing 62 to the eyeglass temple oxygen supply inlet 12. This oxygen then flows through the hollow channel 9 formed in the eyeglass temple 6, in the illustrative example, and through the hinged joint 10 via the sealed interfaces 23, 24, to the hollow channel 9 formed in the bridge portion 32.

In a preferred embodiment of the frame 20, the material from which the frame 20 and/or the temple 2, 6 is made has sufficient structural integrity and/or thickness to allow for formation of a hollow channel 9 with a substantially similar inner diameter to the inner diameter of traditional nasal cannulas, and such that the hollow channel 9 can be routed through the joint end 19 of the temple 6 around the temple hole 25 and fastener 3 forming the hinged joint 10, as shown in FIG. 12. The substantially flat surfaces of the bridge interface 23 and temple interface 24, and the positioning of the sealing element 11 in the groove 30 parallel to the bridge portion 32, are configured such, that with the temple 6 in the open position, e.g., folded away from the bridge portion 32, the O-ring 11 and the temple oxygen outlet 13 are flush with the bridge oxygen inlet 14 of the bridge portion 32 to form a seal at the hinged joint 10 between the hollow channels 9 of the temple 2, 6 and the bridge portion 32.

Advantageously, the sealing element 11, e.g., the O-ring 11, when flush with the bridge interface 23 of the bridge portion 32 provides an air tight seal that prevents and/or dramatically reduces oxygen leakage between the temple oxygen outlet 13 and the bridge inlet 14 as compared to prior art, while at the same time providing easy use of the hinged joint 10, and without interference from the sealing element 11 since the sealing element, e.g., the O-ring 11 is substantially contained within the groove 30 and does not interfere with movement of the temple interface 24 relative to the bridge interface 23, as there are no components protruding from either of the temple or bridge interfaces 24, 23 which must be fitted to each other to form a seal between the hollow channel 9 of the temple 2, 6 and the hollow channel 9 of the bridge bar 15. In the example shown in FIG. 17, the bridge interface 23 is positioned within a recess 28 formed between the hinge flanges 26, such that with the temple 6 in the open position, the joint end 19 of the temple 6 is positioned in the recess 28 and between the hinge flanges 26, providing additional sealing interfaces to prevent leakage of oxygen from the hinged temple joint 10.

FIG. 11 illustrates an exploded view of the eyeglass temple 2, 6 showing the O-ring 11, which is placed in the annular groove 30 surrounding the temple outlet 13. In one example, the thickness of the O-ring 11 is greater than the depth of the annular groove 30 such that when the temple 2, 6 is folded away from the bridge bar 15, as when the frame 20 is worn by a user, the O-ring 11 presses against the bridge interface 23 to completely seal the temple joint 10, such that accidental motion of the user/wearer does not interfere with the operation of the oxygen delivery apparatus 100 while also not protruding from the annular groove 30 enough to interfere with full opening of the temples 2, 6 away from the bridge portion 32.

In one example, the frame 20 and/or the nasal prongs 8 are disposable, such that, in lieu of cleaning or sterilizing the frame 20, the frame 20 and/or the nasal prongs 8 can be periodically replaced to maintain sterility of the replaceable components of the oxygen delivery apparatus 100 during use by the user. In one example, the frame 20 is configured as an eyeglass frame which allows a user to remove lenses from the lens housing 5, for example, prior to disposal of the eyeglass frame 20, such that the removed lenses can be installed into a replacement eyeglass frame 20. In one example, the eyeglass frames 20 and/or the nasal prongs 8 can be cleaned and/or sterilized using ozone, activated oxygen, or such methods as are used for cleaning of CPAP (continuous positive airway pressure) apparatus, to maintain the cleanliness and/or sterility of the oxygen delivery apparatus 100 over time in use. In one example, the eyeglass frame 20 and/or the nasal prongs 8 can be made of a material which can be sterilized by washing using an over the counter cleaner such as soap and water, due to the characteristics of the material, which can include relatively hard plastics or metals with higher mechanical strength and/or stiffness as compared with the polymer-based material from which traditional nasal cannulas are formed. In one example, the material may be a dishwasher-safe material such as a nylon-based material, such that the eyeglass frames 20 and/or nasal prongs 8 formed therefrom could be cleaned in a dishwasher.

Referring now to FIGS. 16 and 17, shown are non-limiting examples of the oxygen delivery apparatus 100C, 100D including a frame 20 which can be worn on the face of a user, and where the frame oxygen inlets 12 are located at the bridge ends 33 of the bridge portion 32, such that, as shown in FIGS. 16 and 17, the frame 20 is fabricated and provided without temples 2, 6. In use, and as illustrated in the exploded view of the apparatus 100 shown in FIG. 17, a cannula tubing assembly 70 can be attached to the frame 20 to form the oxygen delivery apparatus 100C, 100D. The cannula tubing assembly 70 includes, in a non-limiting example, first and second cannula tubes 62 each defining a tubing inlet 72 for connection to an oxygen source, and including a tubing outlet 74 for connection to the frame oxygen inlet 12 of the frame 20. Oxygen is flowed through the cannula tube 62 via a hollow tube channel 66 formed through the length of the cannula tube 62. The tubing inlets 72 can be connected directly to the oxygen source or can be connected, for example, to a Y-connector of an oxygen supply tube connected to the oxygen source. The cannula tubing assembly 70, in the example shown, includes an adjuster 64, which can be slid along the cannula tubes 62 to adjust the length of a temple portion 68 of each cannula tube 62 between the tubing inlet 72 and the adjuster 64, to the length required to retain the oxygen delivery apparatus 100C, 100D on the wearer.

In a non-limiting example, the oxygen delivery apparatus 100C, 100D is worn by the user by attaching the tube outlets 74 to the frame oxygen inlets 12, attaching the nasal prongs 8 to the frame oxygen outlets 7, and placing the apparatus 100C, 100D on the user such that the prong outlets 22 are positioned in the user's nostrils, the nose pads 17 are positioned on the user's nose, and the cannula tubes 62 are positioned along the sides of the user's head, for example, over the user's ears. The length of each of the cannula tubes 62 extending from the adjuster 64 to the bridge ends 33 is adjusted by positioning the adjuster 64 such that the frame 20 is held comfortably and securely on and/or against the user's face when in use. Advantageously, the cannula tubes 62 are attached to the bridge ends 33 such that the cannula tubes 62 are held away from the user's face, so as to not be an irritant to the user's skin. The configuration shown in FIGS. 16, 17 can provide additional adjustability to the user and/or increased comfort to the wearer, for example, when in bed or laying on a pillow, by eliminating the rigid temples 2, 6 from the apparatus 100. In the example apparatus 100C shown in FIG. 16, the frame 20 includes a lens housing 5 and rims 16 such that lenses can be inserted into the frame 20. The lenses can be, as previously described, cosmetic, corrective, tinted, etc., and may be interchangeable, e.g., the rims 16 and/or lens housing may be configured such a pair of lenses can be removed and replaced with another pair of lenses, depending on the needs of the user. Advantageously, a wearer of the example apparatus 100C can benefit from the comfort of the apparatus 100C while having the use of corrective lenses, for example, when in bed.

In the example apparatus 100D shown in FIG. 17, the frame 20 includes the bridge portion 32, which as shown includes the nose pads 17, however does not include the lens housing 5. As such, in this configuration the apparatus 100D can be worn by a user who does not require and/or desire lenses and/or does not wish to wear eyeglass frames without lenses installed. In one example, the apparatus 100D can be configured without the lens housing 5 to avoid contact of the frame 20 with the wearer's cheeks, when such contact may cause irritation. The apparatus 100D shown in FIG. 17 is advantaged by being lighter weight than the apparatus 100C shown in FIG. 16, while providing the structure and support for attaching the cannula tubes 62 to the frame 20 such that the cannula tubes 62 are held away from the user's face, so as to not be an irritant to the user's skin.

The frames 20 shown in FIGS. 16 and 17 can each be fabricated using additive manufacturing processes, as described previously, such that each of the frames 20 shown in FIGS. 16 and 17 can be formed as a monolithic structure, where the hollow channels 9 are contained within the frames 20. In a non-limiting example, the bridge 31 and/or the nose pads 17 can be configured to exert a holding or pinching pressure on the nose, similar to a pince-nez style of glasses, to stabilize the position of the frame 20 on the wearer's nose and/or the positioning of the nasal prongs 8 in the wearer's nostrils. In one example, the bridge 31 and nose pads 17 can be configured as a living spring or hairpin spring such that the nose pads 17 can be flexed outward for positioning on the wearer's nose, and when released, exert a holding pressure on the wearer's nose to retain the frame 20 on the wearer's face.

The examples provided herein are non-limiting. Referring again to FIGS. 16 and 17, in a non-limiting example the temples 2, 6 can be configured such that the joint ends 19 of the temples 2, 6 can be selectively fitted directly onto the frame oxygen inlets 12 of the frame 20 of the oxygen delivery apparatus 100C, 100D. The temples 2, 6 can be configured such that the hollow channel 9 of the temple 2, 6 at the joint end 19 can be friction fit over the frame oxygen inlet 12 to provide a sealed non-hinged joint, such that the temple 2, 6 would extend substantially perpendicular from the bridge portion 32 in a fixed position. In this configuration, the cannula tubes 62 would be attached to the oxygen inlets 12 at the tip ends 18 of the temples 2, 6 to complete the oxygen delivery apparatus 100. Advantageously, the frames 20 shown in FIGS. 16 and 17 could be used alternately with temples 2, 6 attached or detached, for the comfort of the user. In one example, the temples 2, 6 could be attached to the frame for day time use, and the temples 2, 6 could be detached and the cannula tubing attached directly to the frames 20 for use and comfort when the wearer is in bed.

In another non-limiting example, referring again to FIGS. 16 and 17, a pair of temples can be configured to attach to the frame 20 of the oxygen deliver apparatus 100C, 100D, for example, such that each temple is selectively connectable at a bridge end 33 of the bridge portion 32 adjacent to the frame oxygen inlet 12, and such that the cannula tubing 62 can be attached directly to the frame oxygen inlets 12 as previously described for FIGS. 16 and 17. In this example, the temple portion 68 of the cannula tubing 62 can extend adjacent to the temples, such that the visual appearance of the cannula tubing 62 is minimized and/or covered by the temple. In this example, the temple can include clips or otherwise be configured for attachment of the temple portion 68 of the cannula tubes 62 to the temple, to further secure and/or stabilize the position of the cannula tube 62. In the present example, the temples can be selectively attached to the bridge ends 33 of the bridge portion 33 by a fastening mechanism such as a clip, a snap-on element, a magnetic fastener, a screw or other detachable fastener, such that the temples are detachable. In the present example, the temples can be permanently attached to the bridge ends 33, for example, by an adhesive or other permanent fastener. In one configuration, the temples can be formed integrally with the frame 20, by additive manufacturing and/or by molding, as previously described herein. In the present example, the oxygen flows directly from the cannula tubing 62 into the hollow channel 9 of the bridge portion 32 via the frame oxygen inlets 12 at the bridge ends 33, and as such, the temples can be configured without hollow channels 9 formed therein.

Referring now to FIG. 15, a method 50 is illustrated for making an oxygen delivery apparatus 100 as described herein. The method 50 at step 54 includes generating a digital model of the oxygen delivery apparatus 100, which by way of example can be a digital model of one of the apparatus 100A, 100B, 100C, 100D as illustrated in FIGS. 1, 7, 11, 16 and 17, and fabricating at 55 the oxygen delivery apparatus 100, 100A, 100B, 100C, 100D using the digital model. In one example, an additive manufacturing process and the digital model is used to fabricate the eyeglass frame 20 as a monolithic structure, e.g., as a single unit, as shown in FIGS. 1-8. In one example, the eyeglass frame 20 including the temples 2, 6 and the nasal prongs 8 are fabricated as a single monolithic structure using additive manufacturing. In one example, as shown in FIG. 7, the frame 20 and temples 2, 6 are fabricated as a single monolithic structure using additive manufacturing, where in this example the nasal prongs 8 are formed separately and selectively attachable to the frame 20. In one example, the eyeglass frame 20 includes at least one temple 2, 6 attached to the lens housing via a hinged joint, where the temple 2, 6 is configured as a monolithic structure using additive manufacturing, and/or the bridge portion 32 and lens housing 5 is fabricated as a monolithic structure using additive manufacturing, as shown in FIG. 11. In one example, the bridge portion 32 and lens housing 5 as shown in FIG. 16 is fabricated as a monolithic structure using additive manufacturing. In one example, the frame 20 including the bridge portion as shown in FIG. 17 is fabricated as a monolithic structure using additive manufacturing.

As used herein, additive manufacturing includes fabricating processes which create a physical object, such as the oxygen delivery apparatus 100 and/or a component thereof, from a digital model of the apparatus 100 or a component thereof, by the forming subsections of the object as determined from the digital model. In one example, the subsection can be a layer of the object formed by additive manufacturing, which can be additive to other layers of the object formed using the additive manufacturing method. As used herein, the term additive manufacturing method includes but it not limited to 2D printing and 3D printing additive manufacturing techniques. For example, fabricating the oxygen delivery apparatus 100, 100A, 100B, 100C, 100D, collectively referred to herein as the oxygen delivery apparatus 100, and/or one or more of the components 2, 5, 6, 8, 20, 32 thereof, as indicated at steps 55 and 56 of the method 50, can include using one or more, or a combination of additive manufacturing techniques in the categories of powder bed fusion which can include at least one or a combination of direct metal laser melting (DMLM), electron beam melting (EBM), directed metal laser sintering (DMLS), selective laser melting (SLM), selective laser sintering (SLS) and selective hear sintering (SHS), vat photopolymerization which can include at least one or a combination of stereolithography (SLA), digital light processing (DLP), and continuous digital light processing (CDLP), directed energy deposition (DED) which can include at least one of or a combination of laser engineered net shape (LENS), electron beam additive melting (EBAM), and rapid plasma deposition (RPD), material jetting which can include at least one or a combination of drop on demand (DOD) technology, nanoparticle jetting (NPJ), and binder jetting using powder material and a binding agent, material extrusion which can include at least one or a combination of fused deposition modeling (FDM), fused filament fabrication (FFF), or similar methods of 3D printing, and sheet lamination which can include at least one or a combination of laminated object manufacturing (LOM), and ultrasonic additive manufacturing (UAM). The oxygen delivery apparatus 100 and/or one or more of the components 2, 5, 6, 8, 20, 32 thereof can be fabricated from materials which are suitable to the additive manufacturing technique used to form the oxygen delivery apparatus 100 and/or one or more of the components 2, 5, 6, 8, 20, 32 thereof. For example, the oxygen delivery apparatus 100 and/or one or more of the components 2, 5, 6, 8, 20, 32 thereof can be formed from a metal-based material, a polymer-based material, a ceramic-based material and/or a glass-based material, and/or from a composite material such as a polymer glass-filled material, a graphene-embedded plastic, or a composite silicone-based material. By way of non-limiting example, the oxygen delivery apparatus 100 and/or one or more of the components 2, 5, 6, 8, 20, 32 thereof can be formed from nylon-based material, silicone-based material, steel-based material including stainless steel and steel alloys, nickel-based alloys including nickel-copper alloys, titanium, titanium alloys, acetate-based polymers, photopolymer resins, thermoplastic polymers such as ABS, PLA, PVA, polycarbonate, and nylon, and composite materials. The method 50 of fabricating the oxygen delivery apparatus 100 and/or one or more of the components 2, 5, 6, 8, 20, 32 thereof can include post-additive production steps such as finish machining, trimming, polishing, coating, coloring, or other steps as required to finish the component fabricated using additive manufacturing into a finished component.

As shown in FIG. 15 and described previously herein, the method 50 can include, as indicated at 51, measuring and or digitizing physical characteristics and/or features of a subject user, such as head or facial feature dimensions, which can be inputted, at 53, into a system for generating, and/or used in the generation of, the digital model, at 54, of the oxygen delivery apparatus 100 and/or one or more of the components 2, 5, 6, 8, 20, 32 thereof being fabricated using additive manufacturing techniques. The method of measuring and/or digitizing the physical characteristics of the subject user can include physical measurement of the characteristic user using a measurement device, for example, a scale, caliper, angle ruler, protractor, ruler or other physical measurement tool or gauge, and/or can include using measurement device for generating a user image and/or for obtaining one or more image-based measurements, such as a facial scan, photographic imaging, photogrammetry, etc., to obtain measurement information from an image of the subject user. The measurement device can be in communication with a server including one or more algorithms for processing measurement information and data obtained from the measurement device and/or inputted to the server. The measurement information can be stored to a memory in communication with the server. The server can include one or more algorithms for generating one or more digital models using the measurement information, which can include, for example, algorithms for generating a digital model of the subject user's head, face, and/or facial characteristics or elements of the subject user, and algorithms for generating a digital model of an oxygen delivery apparatus 100 and/or one or more of the components 2, 5, 6, 8, 20, 32 thereof using the measurement information. The server can be in communication with an additive manufacturing process, and can further include one or more algorithms for generating instructions to the additive manufacturing process for fabricating the oxygen delivery apparatus 100 and/or one or more of the components 2, 5, 6, 8, 20, 32 thereof using the additive manufacturing process. At 54, the digital model is generated, and as indicated at 55 and 56, the oxygen delivery apparatus 100 and/or one or more of the components 2, 5, 6, 8, 20, 32 thereof is fabricated using an additive manufacturing process and/or technique suitable for the material from which the object is being formed.

In one embodiment of the invention, a computer program is used such that a digital model of numerous styles of eyeglass frames is created or scanned, and components 7, 9, and 12 are automatically generated within the digital model by an algorithm of the computer program in order to convert each of the numerous styles of eyeglass frames into an oxygen delivery apparatus 100. In one example, the method 50 can include, as indicated at 52, the subject user selecting a style of the frame 20, the bridge portion 32, the lens housing 5 and/or the temples 2, 6 where the selection information is inputted with the measurement data to generate the digital model at 54. The method can include, at 57, fabricating lenses for incorporation into the apparatus 100, which as previously described herein, can be corrective or non-corrective lenses. The method can include, at 58, assembling the components 2, 5, 6, 8, 20 to form the oxygen delivery apparatus 100. As previously described, the eyeglass frame 20 can be formed as a monolithic structure such that assembly 58 may comprise attaching nasal prongs 8 to the eyeglass frame 20. In another example, the apparatus 100 including the eyeglass frame 20 and the nasal prongs 8 can be formed as a monolithic structure such that no assembly is required.

The example of method 50 is not limiting. For example, each of the components of the bridge portion 32, the lens housing 5, the temples 2, 6, and the nasal prongs 8 can be manufacturing and or finished in one or more predetermined, e.g., standardized sizes, shapes, styles, colors, and/or other configurations, such as material type, texture, finish, etc., such that a combination of components can be selected and assembled into an oxygen delivery apparatus 100 as described herein, based on the user's requirements, which can include measurements of the user's head, eyes, ears, nose or other facial features, the user's style preferences as to the size, shape, color, material and/or texture of the bridge portion 32, lens housing 5 and temples 2, 6, and nasal prongs 8. For example, the nasal prongs 8 can be provided in a variety of colors and/or textures for matching to the complexion of user.

The method of manufacturing one or more of an eyeglass frame 20, a bridge portion 32, a lens housing 5, a temple 2, 6, and/or a nasal prong 8 is not limited to methods of additive manufacturing. For example, one or more of these components can be fabricated by casting including urethane casting, molding, including injection molding, laser cutting, CNC machining, laser drilling, die cutting, and combinations thereof. In one example, the method of fabricating can include dividing the lens housing 5 into layers, for example, along section A-A of FIG. 1 to provide an anterior portion and a posterior portion of the lens housing 5, and manufacturing each of the anterior and posterior portions separately by additive manufacturing, molding, casting, etc., then sandwiching the anterior and posterior portions together and joining one to the other using an adhesive, bonding agent, welding, or other joining method sufficient to form a sealed hollow channel 9 therebetween. For example, a combination of additive and non-additive manufacturing methods can be used to fabricate the oxygen delivery apparatus 100. In one example, a tubular element defining the hollow channel 9 can be fabricated using an additive manufacturing method, for example, 3D printing, and the tubular element can be inserted into a mold such that the bridge portion 32, the lens housing 5 and/or the temples 2, 6 can be molded or cast around the tubular element.

Various modifications to the description of the disclosed embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein. For example, the shape and size of the hollow channels 9 can be modified and/or optimized based on the style of the frame 20, the bridge portion 32, the lens housing 5 and/or the temples 2, 6, and/or for fluid flow considerations. In one example, the hollow channel 9 has an inner diameter configured to provide an oxygen flow rate substantially equivalent to the oxygen flow rate provided by a comparable nasal cannula. For example, the hollow channel 9, frame oxygen inlet 12, frame oxygen outlet 7 and nasal prong 8 can each have an inner diameter of 3.5 mm such that the hollow channel 9 provides an oxygen flow rate comparable to a high flow nasal cannula. In one example, the hollow channels 9 can be cylindrical in shape and can have an oval cross-section, rather than a circular cross-section, to modify the fluid dynamics of oxygen flow through the hollow channels 9 by increasing the surface area and cross-sectional area of the hollow oval channel 9 relative to a circular channel 9, to increase flow rate while maintaining a flatter profile, e.g., a thinner cross-section, of the lens housing 5 and/or temple 2, 6 as would be required to house a circular channel having the same surface area and cross-sectional area as the oval channel. In one example, a first portion of the hollow channel 9 has a first cross-sectional area and a second portion of the hollow channel 9 has a second cross-sectional area which is different from the first cross-sectional area, to modify the fluid dynamics of oxygen flow through the first and second portions of the hollow channel 9.

In the paragraphs above, the oxygen delivery apparatus 100 is described in detail by way of example with reference to the attached drawings. Throughout this description, the preferred embodiment and examples shown should be considered as exemplars, rather than as limitations on the present disclosure. The oxygen delivery apparatus 100 disclosed herein may, however, be embodied in many different forms and should not be construed as limited to the embodiments set forth herein. These embodiments are provided so that this disclosure will be thorough and complete and will fully convey the scope of the disclosure to those of ordinary skill in the art. Moreover, all statements herein reciting embodiments of the oxygen delivery apparatus 100 disclosed herein, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and such as represent conceptual views or processes illustrating systems and methods embodying oxygen delivery apparatus 100 disclosed herein. Those of ordinary skill in the art further understand that the exemplary hardware, software, processes, methods, and/or operating systems described herein are for illustrative purposes and, thus, are not intended to be limited to any particular named manufacturer.

Various modifications and alterations of the oxygen delivery apparatus 100 disclosed herein will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language. Additionally, with regard to flow diagrams, operational descriptions and method claims, the order in which the steps are presented herein shall not mandate that various embodiments be implemented to perform the recited functionality in the same order unless the context dictates otherwise.

While various embodiments of the oxygen delivery apparatus 100 disclosed herein have been described above, it should be understood that they have been presented by way of example only, and not of limitation. The various diagrams may depict an example architectural or other configuration for the present teachings, which is done to aid in understanding the features and functionality that may be included in the invention. The oxygen delivery apparatus 100 disclosed herein is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present teachings. Also, a multitude of different constituent module names other than those depicted herein may be applied to the various partitions.

Although the oxygen delivery apparatus is described herein in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the oxygen delivery apparatus, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the such as; the term "example" is used to provide exemplary instances of the item in discussion, not an exhaustive or limiting list thereof; the terms "a" or "an" should be read as meaning "at least one," "one or more" or the such as; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Hence, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other such as phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

The invention claimed is:

1. An oxygen delivery apparatus wearable by user, the oxygen delivery apparatus comprising:
   a frame including:
      a bridge portion, wherein the bridge portion includes a first bridge end and a second bridge end;
      first and second nose pads operatively connected to the bridge portion;
      a first oxygen inlet, wherein the first bridge end defines the first oxygen inlet;
      a first oxygen outlet defined by the first nose pad;
      a first hollow channel contained by the frame; and
      a first temple configured to be selectively attached to the first bridge end;
   wherein:
      the first oxygen inlet and the first oxygen outlet are in fluid communication via the first hollow channel; and
      the frame is formed as a monolithic structure.

2. The oxygen delivery apparatus of claim 1, wherein:
   the frame further includes:
      a second oxygen inlet;
      a second oxygen outlet defined by the second nose pad;
      a second hollow channel contained by the frame; and
   wherein the second oxygen inlet and the second oxygen outlet are in fluid communication via the second hollow channel.

3. The oxygen delivery apparatus of claim 1, further comprising:
   the first nose pad including the first oxygen outlet; and
   the second nose pad including the second oxygen outlet.

4. The oxygen delivery apparatus of claim 1, further comprising:
   a first nasal prong defining a prong outlet;
   wherein the first nasal prong is operatively connected to the first oxygen outlet such that the prong outlet is in fluid communication with the first hollow channel.

5. The oxygen delivery apparatus of claim 4, wherein the frame and the first nasal prong are configured such that when the oxygen delivery apparatus is worn by the user, the prong outlet is positioned within a nostril of the user.

6. The oxygen delivery apparatus of claim 4, wherein the first nasal prong is integral to the frame such that the monolithic structure includes the frame and the first nasal prong.

7. The oxygen delivery apparatus of claim 4, wherein the first nasal prong is configured to be selectively attached to and selectively detached from the first oxygen outlet.

8. The oxygen delivery apparatus of claim 7, wherein:
   the first nasal prong includes a prong inlet defining a vee slot; and
   the first nasal prong is attachable to the first oxygen outlet by:
      inserting the prong inlet with the vee slot in a collapsed state into the first oxygen outlet; and
      releasing the vee slot from the collapsed state such that the prong inlet is retained in the first oxygen outlet.

9. The oxygen delivery apparatus of claim 4, wherein the first nasal prong includes:
   a contoured portion defining the prong outlet;
   a linear portion;
   wherein with the first nasal prong operatively connected to the first oxygen outlet, the linear portion is intermediate the contoured portion and the first oxygen outlet.

10. The oxygen delivery apparatus of claim 1, further comprising:
    a lens housing operatively connected to the bridge portion;
    wherein the lens housing and the bridge portion are configured to house at least one lens in the frame.

11. The oxygen delivery apparatus of claim 1, wherein the first oxygen inlet is configured to receive a cannula tubing;

wherein the cannula tubing is configured to be selective connected to a source of gaseous oxygen; and wherein the first oxygen inlet is configured to be in fluid communication with the source of gaseous oxygen via the cannula tubing.

12. The oxygen delivery apparatus of claim 1, further comprising:
a bridge defined by the bridge portion;
a living spring defined by the first and second nose pads and the bridge; and
such that when the oxygen delivery apparatus is worn by the user, the living spring is configured to exert a holding pressure on a nose of the user to retain the frame to the user.

13. The oxygen delivery apparatus of claim 1, wherein the monolithic structure is formed by additive manufacturing.

14. The oxygen delivery apparatus of claim 1, wherein:
the frame further includes:
the first temple connected to the bridge portion to define a temple joint;
the first temple including a tip end defining the first oxygen outlet;
wherein the first hollow channel is continuous through the temple joint and the first temple such that the first oxygen inlet and the first oxygen outlet are in fluid communication via the first hollow channel; and
wherein the first temple is integral to the frame such that the monolithic structure includes the frame, the first temple joint and the first temple.

15. The oxygen delivery apparatus of claim 1, further comprising:
the first bridge end including a substantially flat bridge interface defining the first oxygen inlet;
the first temple including:
a first temple end including a substantially flat temple interface defining a second oxygen outlet;
a second temple end defining a second oxygen inlet;
a second hollow channel contained by the first temple;
wherein the second oxygen inlet and the second oxygen outlet are in fluid communication via the second hollow channel;
wherein the first temple end is hingedly attached to the first bridge end to define a hinged joint;
wherein the first temple can be articulated via the hinged joint between an open position and a closed position;
wherein with the first temple in the open position the substantially flat temple interface and the substantially flat bridge interface are in sealing contact such that the second oxygen inlet and the first oxygen outlet are in fluid communication via a temple joint.

16. The oxygen delivery apparatus of claim 15, wherein the hinged joint further comprises:
a sealing element disposed between the first temple end and the first bridge end;
wherein the first hollow channel is in fluid communication with the second hollow channel via the sealing element.

17. The oxygen delivery apparatus of claim 1, further comprising:
the first temple including:
a second oxygen inlet;
a second oxygen outlet;
a second hollow channel contained by the first temple;
wherein the second oxygen inlet and the second oxygen outlet are in fluid communication via the second hollow channel;
wherein the first temple is configured to be selectively attached to the first bridge end by attachment of the first oxygen outlet and the first oxygen inlet;
a temple joint formed by attachment of the first oxygen outlet and the first oxygen inlet;
wherein the first hollow channel and the second hollow channel are in fluid communication via the temple joint.

18. A method for forming an oxygen delivery apparatus wearable by a user, the method comprising:
forming, using an additive manufacturing process, a frame including:
a bridge portion;
first and second nose pads operatively connected to the bridge portion;
a first oxygen inlet;
a first oxygen outlet defined by the first nose pad;
a first hollow channel contained by the frame;
measuring, using a measurement device, at least one of a head feature and a facial feature of a user to generate at least one measurement;
generating, using a server, a digital model of the frame using the at least one measurement; and
forming the frame using the digital model;
wherein:
the first oxygen inlet and the first oxygen outlet are in fluid communication via the first hollow channel; and
the frame is formed as a monolithic structure.

* * * * *